(12) United States Patent
Matsumura et al.

(10) Patent No.: US 11,377,413 B2
(45) Date of Patent: Jul. 5, 2022

(54) METHOD FOR PRODUCING PROSTAGLANDIN DERIVATIVE

(71) Applicant: AGC INC., Chiyoda-ku (JP)

(72) Inventors: Yasushi Matsumura, Chiyoda-ku (JP); Yusuke Nagai, Chiyoda-ku (JP); Yu Yamaguchi, Chiyoda-ku (JP); Lanfang Wang, Chiyoda-ku (JP)

(73) Assignee: AGC INC., Chiyoda-ku (JP)

( * ) Notice: Subject to any disclaimer, the term of this patent is extended or adjusted under 35 U.S.C. 154(b) by 215 days.

(21) Appl. No.: 16/852,622

(22) Filed: Apr. 20, 2020

(65) Prior Publication Data

US 2020/0239397 A1 Jul. 30, 2020

Related U.S. Application Data

(63) Continuation of application No. PCT/JP2018/039794, filed on Oct. 26, 2018.

(30) Foreign Application Priority Data

Oct. 31, 2017 (JP) ................ JP2017-210311

(51) Int. Cl.
*C07C 51/373* (2006.01)

(52) U.S. Cl.
CPC ................ *C07C 51/373* (2013.01)

(58) Field of Classification Search
CPC ........................................... C07C 51/373
USPC ....................................................... 562/503
See application file for complete search history.

(56) References Cited

U.S. PATENT DOCUMENTS

| | | | |
|---|---|---|---|
| 3,931,296 A | 1/1976 | Hayashi et al. | |
| 4,052,512 A | 10/1977 | Hayashi et al. | |
| 4,073,934 A | 2/1978 | Skuballa et al. | |
| 4,235,930 A | 11/1980 | Skuballa et al. | |
| 4,294,849 A | 10/1981 | Hayashi et al. | |

FOREIGN PATENT DOCUMENTS

| CN | 104284886 B | 8/2016 |
|---|---|---|
| JP | 50-71649 A | 6/1975 |
| JP | 50-116452 A | 9/1975 |
| JP | 51-131860 A | 11/1976 |
| JP | 52-85151 A | 7/1977 |
| JP | 53-149954 A | 12/1978 |
| JP | 54-012352 A | 1/1979 |
| JP | 55-100360 A | 7/1980 |
| JP | 06-199779 A | 7/1994 |
| JP | 10-017561 A | 1/1998 |
| WO | WO 2014/040457 A1 | 3/2014 |
| WO | WO 2017/195762 A1 | 11/2017 |

OTHER PUBLICATIONS

Annals New York Academy of Sciences, vol. 180, 1971, pp. 181-199.
Prostaglandins, vol. 8, 1974, pp. 341-344.
International Search Report dated Dec. 18, 2018 in PCT/JP2018/039794 filed on Oct. 26, 2018, citing documents AA & AO-AR therein, 2 pages.

*Primary Examiner* — Ana Z Muresan
(74) *Attorney, Agent, or Firm* — Oblon, McClelland, Maier & Neustadt, L.L.P.

(57) ABSTRACT

The present invention relates to a novel production method of a novel prostaglandin derivative or a pharmaceutically acceptable salt thereof useful as a medicament, and an intermediate therefor. According to the present invention, a production method of a novel prostaglandin derivative or a pharmaceutically acceptable salt thereof including a conversion step from a compound represented by the following formula 3 to a compound represented by the formula 1 can be provided:

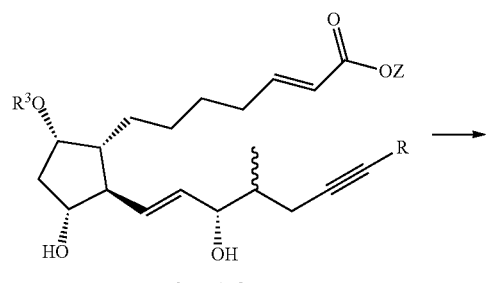

formula 3

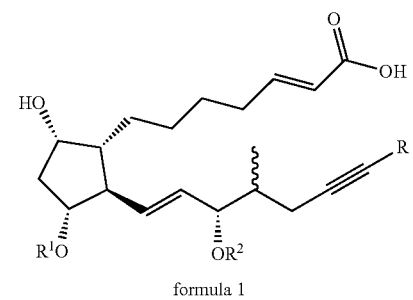

formula 1 wherein each symbol is as defined in the DESCRIPTION.

13 Claims, No Drawings

METHOD FOR PRODUCING PROSTAGLANDIN DERIVATIVE

TECHNICAL FIELD

The present invention relates to a novel production method of a novel prostaglandin derivative having an alkynyl group on the ω-chain of a prostaglandin, a pharmaceutically acceptable salt thereof, or a cyclodextrin clathrate compound thereof, particularly, a novel prostaglandin derivative having a double bond at the 2-position of a prostaglandin and an alkynyl group on the ω-chain, and an intermediate thereof.

BACKGROUND ART

Natural prostaglandins (hereinafter prostaglandin is to be indicated as PG) are a group of bioactive substances synthesized in the body, and regulate cellular functions of each tissue of the body as a topical hormone having various physiological activities. In particular, PGE1s, which are one kind of natural PGs, have, for example, a vasodilating action, an angiogenesis action, a platelet aggregation suppressive action, and an epithelial regeneration promoting action. They are used as an antiplatelet agent, an agent for improving peripheral blood flow disorders and the like in the drug therapy of the above-mentioned diseases. While PGEs may be applicable to other indications, natural PGEs are extremely unstable chemically and metabolically. Thus, the development of PGE derivatives which are more stable and effective, and cause fewer side effects has been extensively studied.

A PG derivative having a double bond at the 2-position of PG and a production method thereof are reported in the following patent documents 1-5 and non-patent documents 1 and 2. In addition, a PG derivative having an alkynyl group in the ω-chain of PG and a production method thereof are reported in the following patent documents 6 and 7.

DOCUMENT LIST

Patent Documents

Patent document 1: JP-A-50-71649
Patent document 2: JP-A-50-116452
Patent document 3: JP-A-52-85151
Patent document 4: JP-A-53-149954
Patent document 5: JP-A-55-100360
Patent document 6: JP-A-51-131860
Patent document 7: JP-A-54-12352

Non-Patent Documents

Non-patent document 1: Ann. Acad. N. Y. Sci., 1971, vol. 180, p. 181.
Non-patent document 2: Prostaglandins, 1974, vol. 8, p. 341.

SUMMARY OF THE INVENTION

Problems to be Solved by the Invention

The present invention aims to provide a novel production method of a novel prostaglandin derivative useful as a therapeutic agent for a blood flow disorder, and the like.

Means of Solving the Problems

The present inventors synthesized a novel prostaglandin derivative and studied same to clarify properties and physiological activity thereof. As a result, they have found a high-yielding method for producing a compound represented by the following formula 2 or a pharmaceutically acceptable salt thereof which is useful as an antiplatelet agent or a blood flow improving agent. In addition, they have found a novel compound represented by the following formula 3 and a novel compound represented by the following formula 4 that are useful as intermediates for producing a compound represented by the following formula 2 or a pharmaceutically acceptable salt thereof, and completed the present invention.

Accordingly, the present invention provides the following.

[1] A compound represented by the formula 3:

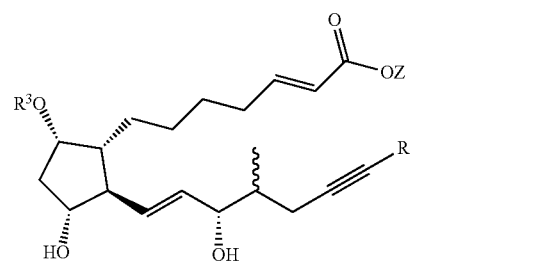

formula 3 wherein, in the formula 3, R is an alkyl group having 2 to 3 carbon atoms, a substituted alkyl group having 2 to 3 carbon atoms, a cycloalkyl group having 3 to 5 carbon atoms, or a substituted cycloalkyl group having 3 to 5 carbon atoms;

$R^3$ is a hydroxy-protecting group;

a methyl group bonded by a wavy line is a methyl group having α-configuration, β-configuration or a mixed configuration of α-configuration and β-configuration; and Z is an alkyl group having 1 to 4 carbon atoms or a substituted alkyl group having 1 to 4 carbon atoms.

[2] A method for producing a compound represented by the formula 1 or a pharmaceutically acceptable salt thereof, comprising protecting a hydroxy group of a compound represented by the formula 3, and converting same to a compound represented by the above-mentioned formula 1 by subsequently removing $R^3$ and hydrolyzing a $CO_2Z$ group:

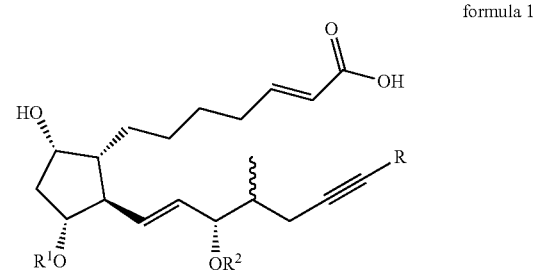

formula 1 wherein, in the formula 1, R is an alkyl group having 2 to 3 carbon atoms, a substituted alkyl group having 2 to 3 carbon atoms, a cycloalkyl group having 3 to 5 carbon atoms or a substituted cycloalkyl group having 3 to 5 carbon atoms; $R^1$ and $R^2$ are each independently a hydroxy-protecting group; and a methyl group bonded by a wavy line is a methyl group having α-configuration, β-configuration or a mixed configuration of α-configuration and β-configuration,

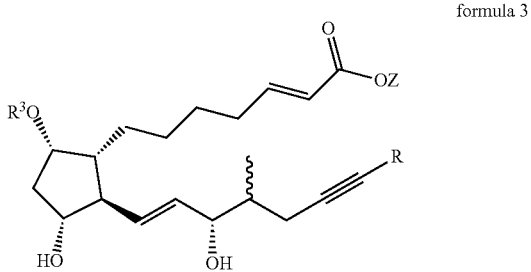

formula 3 wherein, in the formula 3, $R^3$ is a hydroxy-protecting group different from $R^1$ and $R^2$;

Z is an alkyl group having 1 to 4 carbon atoms or a substituted alkyl group having 1 to 4 carbon atoms; and R and a methyl group bonded by a wavy line are as defined above.

[3] A method for producing a compound represented by the formula 2 or a pharmaceutically acceptable salt thereof, comprising oxidizing a hydroxy group of the compound represented by the formula 1 or a pharmaceutically acceptable salt thereof of the above-mentioned [2], and removing $R^1$ and $R^2$:

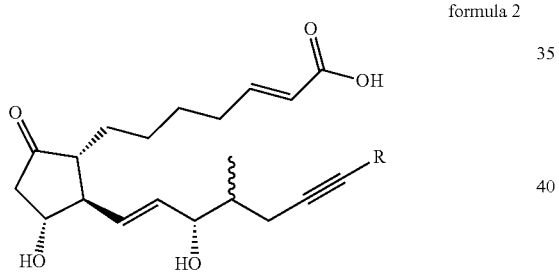

formula 2 wherein, in the formula 2, R and a methyl group bonded by a wavy line are as defined in [2].

[4] The production method of the above-mentioned [2], wherein the compound represented by the above-mentioned formula 3 is produced by reducing a carbonyl group of a compound represented by the formula 4 and then removing $R^4$:

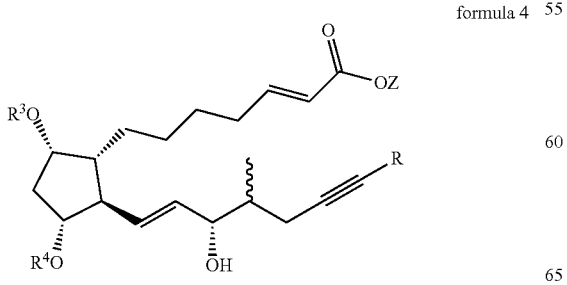

formula 4 wherein, in the formula 4, $R^3$, R, a methyl group bonded by a wavy line and Z are as defined in [2]; and $R^4$ is a hydroxy-protecting group different from $R^3$.

[5] The production method of the above-mentioned [4], wherein the compound represented by the above-mentioned formula 4 is obtained by oxidizing a hydroxy group of the compound represented by the formula 5 to convert same to the corresponding aldehyde, and reacting the compound with a compound represented by the formula 6:

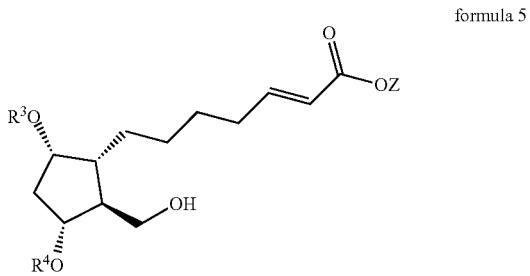

formula 5 wherein, in the formula 5, $R^3$, $R^4$, and Z are as defined in [4],

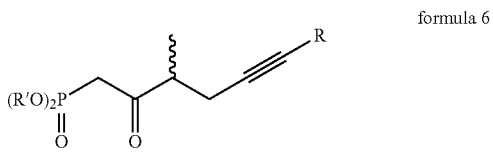

formula 6 wherein, in the formula 6, R' is an alkyl group having 1 to 4 carbon atoms, and R and a methyl group bonded by a wavy line are as defined in [4].

[6] The production method of the above-mentioned [5], wherein a compound represented by the above-mentioned formula 5 is obtained by arylselenylating a compound represented by the formula 7 to convert same to a compound represented by the formula 8, protecting a hydroxy group, removing $R^5$ to convert the compound to a compound represented by the formula 9, and oxidatively eliminating an arylselenyl group to introduce a double bond:

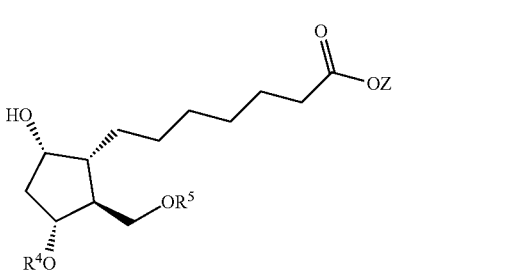

formula 7 wherein, in the formula 7, $R^4$ and Z are as defined in [5]; and $R^5$ is a hydroxy-protecting group different from $R^3$ and $R^4$,

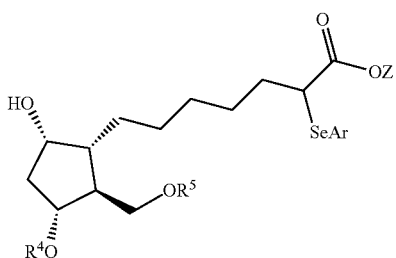

formula 8 wherein, in the formula 8, $R^4$, $R^5$ and Z are as defined above; and

Ar is an aryl group or a substituted aryl group,

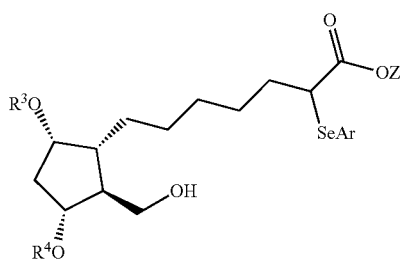

formula 9 wherein, in the formula 9, $R^3$ is as defined in [5]; and $R^4$, Ar and Z are as defined above.

[7] A compound represented by the formula 4.

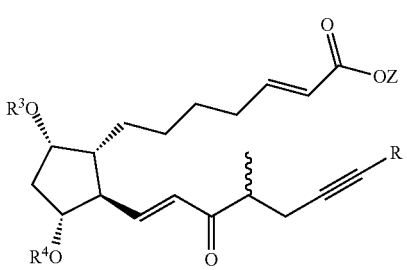

formula 4 wherein, in the formula 4, R is an alkyl group having 2 to 3 carbon atoms, a substituted alkyl group having 2 to 3 carbon atoms, a cycloalkyl group having 3 to 5 carbon atoms, or a substituted cycloalkyl group having 3 to 5 carbon atoms;

$R^3$ is a hydroxy-protecting group;

$R^4$ is a hydroxy-protecting group different from $R^3$; a methyl group bonded by a wavy line is a methyl group having α-configuration, β-configuration or a mixed configuration of α-configuration and β-configuration; and Z is an alkyl group having 1 to 4 carbon atoms or a substituted alkyl group having 1 to 4 carbon atoms.

[8] A method for producing a compound represented by the formula 3, comprising reducing a carbonyl group of the compound represented by the formula 4, and removing $R^4$:

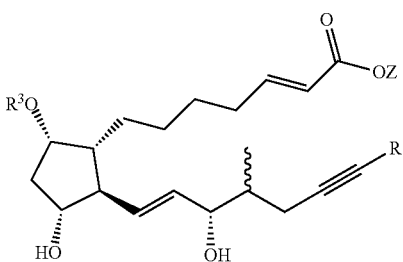

formula 3 wherein, in the formula 3, R is an alkyl group having 2 to 3 carbon atoms, a substituted alkyl group having 2 to 3 carbon atoms, a cycloalkyl group having 3 to 5 carbon atoms, or a substituted cycloalkyl group having 3 to 5 carbon atoms;

$R^3$ is a hydroxy-protecting group;

a methyl group bonded by a wavy line is a methyl group having α-configuration, β-configuration or a mixed configuration of α-configuration and β-configuration; and Z is an alkyl group having 1 to 4 carbon atoms or a substituted alkyl group having 1 to 4 carbon atoms,

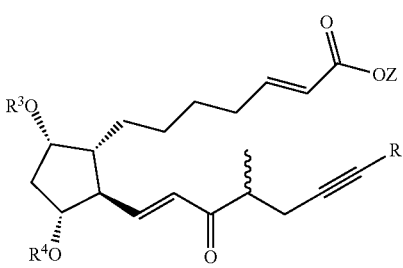

formula 4 wherein, in the formula 4, $R^3$, R, a methyl group bonded by a wavy line, and Z are as defined above; and $R^4$ is a hydroxy-protecting group different from $R^3$.

[9] A method for producing a compound represented by the formula 4, comprising oxidizing a hydroxy group of a compound represented by the formula 5 to convert the compound to the corresponding aldehyde, and reacting same with a compound represented by the formula 6

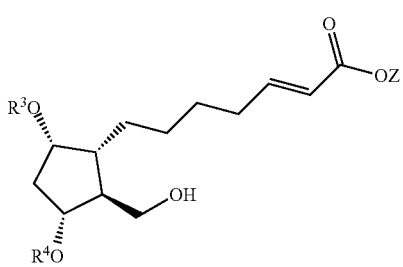

formula 5 wherein, in the formula 5, $R^3$ is a hydroxy-protecting group; $R^4$ is a hydroxy-protecting group different from $R^3$; and Z is an alkyl group having 1 to 4 carbon atoms or a substituted alkyl group having 1 to 4 carbon atoms,

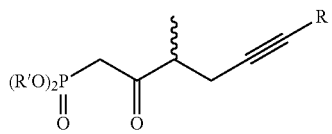

formula 6 wherein, in the formula 6, R' is an alkyl group having 1 to 4 carbon atoms, R is an alkyl group having 2 to 3 carbon atoms, a substituted alkyl group having 2 to 3 carbon atoms, a cycloalkyl group having 3 to 5 carbon atoms, or a substituted cycloalkyl group having 3 to 5 carbon atoms, and a methyl group bonded by a wavy line is a methyl group having α-configuration, β-configuration or a mixed configuration of α-configuration and β-configuration,

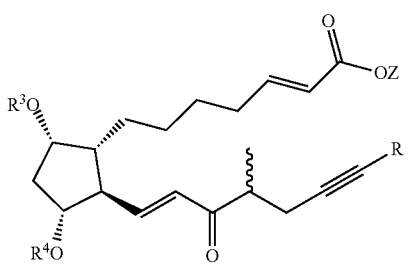

formula 4 wherein, in the formula 4, $R^3$, $R^4$, R, a methyl group bonded by a wavy line, and Z are as defined above.

[10] A method for producing a compound represented by the formula 2 or a pharmaceutically acceptable salt thereof, comprising arylselenylating a compound represented by the formula 7 to convert same to a compound represented by the formula 8, protecting a hydroxy group of the compound represented by the formula 8, removing $R^5$ to convert the compound to a compound represented by the formula 9, oxidatively eliminating an arylselenyl group of the compound represented by the formula 9 to introduce a double bond and convert the compound to a compound represented by the formula 5, oxidizing a hydroxy group of the compound represented by the formula 5 to convert same to the corresponding aldehyde, reacting same with a compound represented by the formula 6 to convert the compound to a compound represented by the formula 4, reducing a carbonyl group of the compound represented by the formula 4, removing $R^4$ to convert the compound to a compound represented by the formula 3, protecting a hydroxy group of the compound represented by the formula 3, subsequently removing $R^3$ and hydrolyzing a $CO_2Z$ group to convert the compound to a compound represented by the formula 1 or a pharmaceutically acceptable salt thereof, and oxidizing a hydroxy group of the compound represented by the formula 1 or a pharmaceutically acceptable salt thereof, and removing $R^1$ and $R^2$ to convert the compound to a compound represented by the above-mentioned formula 2 or a pharmaceutically acceptable salt thereof,

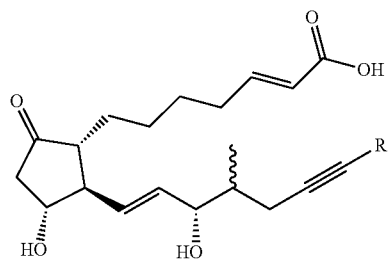

formula 2 wherein, in the formula 2, R is an alkyl group having 2 to 3 carbon atoms, a substituted alkyl group having 2 to 3 carbon atoms, a cycloalkyl group having 3 to 5 carbon atoms or a substituted cycloalkyl group having 3 to 5 carbon atoms; and a methyl group bonded by a wavy line is a methyl group having α-configuration, β-configuration or a mixed configuration of α-configuration and β-configuration,

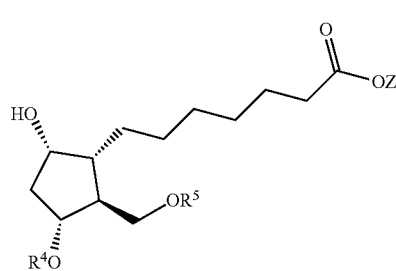

formula 7 wherein, in the formula 7, Z is an alkyl group having 1 to 4 carbon atoms or a substituted alkyl group having 1 to 4 carbon atoms;

$R^4$ is a hydroxy-protecting group; and $R^5$ is a hydroxy-protecting group different from $R^3$ and $R^4$,

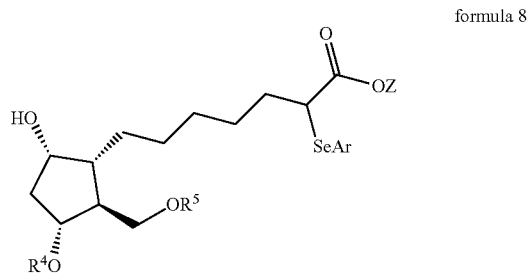

formula 8 wherein, in the formula 8, $R^4$, $R^5$ and Z are as defined above; and

Ar is an aryl group or a substituted aryl group,

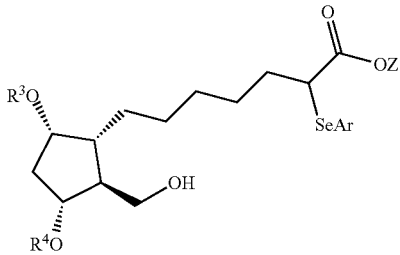
formula 9 wherein, in the formula 9, $R^4$, Ar and Z are as defined above; and $R^3$ is a hydroxy-protecting group different from $R^4$,

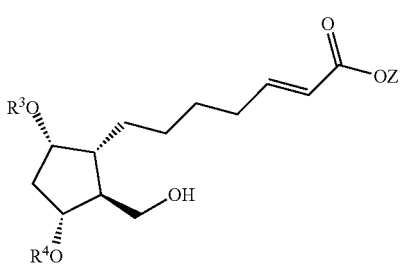
formula 5 wherein, in the formula 5, $R^3$, $R^4$ and Z are as defined above,

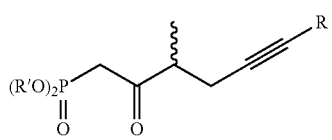
formula 6 wherein, in the formula 6, R' is an alkyl group having 1 to 4 carbon atoms, and R and a methyl group bonded by a wavy line are as defined above,

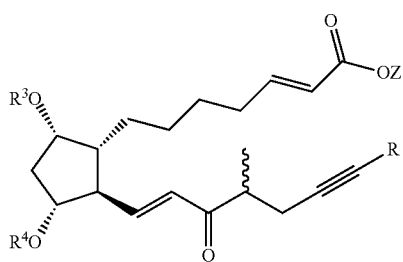
formula 4 wherein, in the formula 4, R, $R^3$, $R^4$, a methyl group bonded by a wavy line and Z are as defined above,

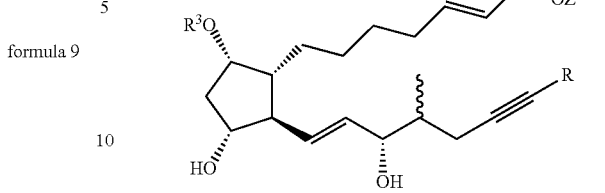
formula 3 wherein, in the formula 3, R, $R^3$, a methyl group bonded by a wavy line and Z are as defined above,

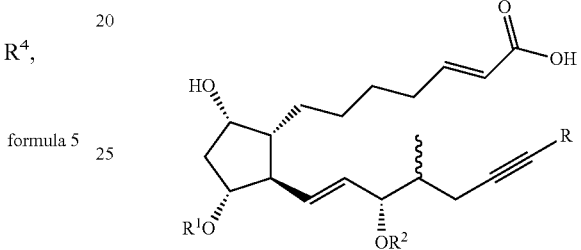
formula 1 wherein, in the formula 1, $R^1$ and $R^2$ are each independently a hydroxy-protecting group; and R and a methyl group bonded by a wavy line are as defined above.

[11] The compound of the above-mentioned [1], wherein, in the formula 3, the methyl group bonded by a wavy line is as defined in the above-mentioned [1], R is an ethyl group or a cyclopropyl group, $R^3$ is an acetyl group, and Z is a methyl group.

[12] The compound of the above-mentioned [7], wherein, in the formula 4, the methyl group bonded by a wavy line is as defined in the above-mentioned [7], R is an ethyl group or a cyclopropyl group, $R^3$ is an acetyl group, $R^4$ is a 2-tetrahydropyranyl group, and Z is a methyl group.

[13] The compound of the above-mentioned [2], wherein the methyl group bonded by a wavy line in the formula 1 is as defined in the above-mentioned [2], R is an ethyl group or a cyclopropyl group, $R^1$ and $R^2$ are each a 2-tetrahydropyranyl group, the methyl group bonded by a wavy line in the formula 3 is as defined in the above-mentioned [2], R is as defined in the formula 1, $R^3$ is an acetyl group, and Z is a methyl group.

Effect of the Invention

According to the production method of the present invention, a novel prostaglandin derivative useful as a therapeutic agent for blood flow disorders can be produced by convenient operations and in a high yield via a compound which is easy to handle. In addition, the present invention can provide a novel intermediate useful for the production method.

DESCRIPTION OF EMBODIMENTS

The embodiments of the present invention are explained in detail in the following.

[Definition of Terms]

The terms in the present specification mean the following.

The numerical range shown with "-" indicates a range containing the numerical values before and after "-" respectively as the minimum value and the maximum value.

A compound represented by a formula is indicated by "compound" followed by the formula number. For example, a compound represented by the formula 1 is indicated as "compound (1)".

The "alkyl group having 2 to 3 carbon atoms" is a linear or branched chain alkyl group having 2 to 3 carbon atoms, and exemplified by an ethyl group, a propyl group, and an isopropyl group.

The "alkyl group having 1 to 4 carbon atoms" is a linear or branched chain alkyl group having 1 to 4 carbon atoms, and exemplified by a methyl group, an ethyl group, a propyl group, an isopropyl group, a butyl group, an isobutyl group, a sec-butyl group, and a tert-butyl group.

The "alkyl group having 1 to 8 carbon atoms" is a linear or branched chain alkyl group having 1 to 8 carbon atoms, and exemplified by a methyl group, an ethyl group, a propyl group, an isopropyl group, a butyl group, an isobutyl group, a sec-butyl group, a tert-butyl group, a pentyl group, a hexyl group, a heptyl group, and an octyl group.

The "cycloalkyl group having 3 to 5 carbon atoms" is a cycloalkyl group having 3 to 5 carbon atoms, and exemplified by a cyclopropyl group, a cyclobutyl group, and a cyclopentyl group.

The "substituent" is a known substituent and means a group selected from the groups that do not participate in the reactions in the production method of the present invention.

The "substituted alkyl group having 2 to 3 carbon atoms" and the "substituted alkyl group having 1 to 4 carbon atoms" mean groups in which one or more hydrogen atoms of the above-mentioned alkyl group is/are substituted by substituent(s). The substituent is selected from the groups that do not participate in the reactions in the production method of the present invention, and exemplified by a halogen atom, an alkoxy group having 1 to 8 carbon atoms, and an aryl group.

The "substituted cycloalkyl group having 3 to 5 carbon atoms" is a cycloalkyl group having 3 to 5 carbon atoms constituting the ring, not including the carbon number of the substituent. Examples of the substituted cycloalkyl group having 3 to 5 carbon atoms include a 2-methylcyclopropyl group and a 1-methylcyclopentyl group.

The "halogen atom" is an iodine atom, a bromine atom, a chlorine atom or a fluorine atom.

The "alkoxy group having 1 to 8 carbon atoms" is an alkyl group having 1 to 8 carbon atoms and having an oxygen atom bonded to the bonding terminal, and exemplified by a methoxy group, an ethoxy group, a propyloxy group, an isopropyloxy group, a butoxy group, an isobutyloxy group, a sec-butyloxy group, a tert-butyloxy group, and a hexyloxy group.

The "aryl group" is an aromatic hydrocarbon group having 6 to 18 carbon atoms, and exemplified by a phenyl group, a naphthyl group, and an anthryl group, and a phenyl group is preferable.

The "substituted aryl group" is the above-mentioned aryl group substituted with one or more hydrogen atoms. The substituent is selected from the groups that do not participate in the reactions in the production method of the present invention, and exemplified by a halogen atom, an alkyl group having 1 to 8 carbon atoms, an alkoxy group having 1 to 8 carbon atoms, and an alkylenedioxy group having 1 to 3 carbon atoms (e.g., methylenedioxy group, ethylenedioxy group etc.). Examples of the substituted aryl group include a 2-methylphenyl group, a 3-methylphenyl group, a 4-methylphenyl group, a 2,4-di-tert-butylphenyl group, a 4-methoxyphenyl group, and a 4-chlorophenyl group.

The "hydroxy-protecting group" is a protecting group that is not deprotected by each reaction used in the production method of the present invention, but deprotected by other chemical methods (e.g., chemical method generally used in synthetic organic chemistry, such as hydrogenolysis, hydrolysis, electrolysis, photolysis) to be a hydroxy group (—OH). The protecting group is selected from known or well-known protecting groups that are generally known as hydroxy-protecting groups. For example, they are known to those of ordinary skill in the art from "Protective Groups in Organic Synthesis" (T. W. Greene et. al., John Wiley & Sons, inc., 2007). Specifically, for example, acyl group, tri-organosilyl group, alkoxyalkyl group, monovalent group having cyclic ether structure and the like can be mentioned. As the acyl group, acetyl group, benzoyl group, chloroacetyl group, dichloroacetyl group, trichloroacetyl group, trifluoroacetyl group, propionyl group, and pivaloyl group are preferable. As the tri-organosilyl group, a group in which three of alkyl group, aryl group, aralkyl group and alkoxy group are bonded to the silicon atom is preferable. For example, tert-butyldimethylsilyl group, tert-butyldiphenylsilyl group, trimethylsilyl group, triethylsilyl group, triphenylsilyl group, or triisopropylsilyl group is more preferable. As the alkoxyalkyl group, methoxymethyl group, benzyloxymethyl group, tert-butoxymethyl group, 2-methoxyethoxymethyl group, 1-ethoxyethyl group, and 1-methyl-1-methoxyethyl group are preferable. As the monovalent group having a cyclic ether structure, tetrahydropyranyl group, and tetrahydrofuranyl group are preferable. Acetyl group, benzoyl group, tetrahydropyranyl group, tert-butyldimethylsilyl group, and tert-butyldiphenylsilyl group are particularly preferable.

The hydroxy-protecting groups can be deprotected easily by a conventional method. Specifically, for example, they can be deprotected by the methods described in, for example, "Protective Groups in Organic Synthesis" (T. W. Greene et. al., John Wiley & Sons, inc., 2007).

Deprotection of the protected hydroxy group is sometimes indicated as, for example, "$R^4$ is removed" from $OR^4$. The group after removal of $R^4$ in this case is a hydroxy group (—OH).

The "pharmaceutically acceptable salt" is, for example, a salt derived from a nontoxic inorganic base or a salt derived from a nontoxic organic base, and a salt derived from a nontoxic inorganic base is preferable.

Examples of the salt derived from an inorganic base include sodium salt, potassium salt, calcium salt, magnesium salt, zinc salt, aluminum salt, ammonium salt, as well as lithium salt, copper salt, ferric salt, ferrous salt, manganese salt, manganous salt and the like, and sodium salt, potassium salt, calcium salt, magnesium salt and ammonium salt are preferable, and sodium salt and potassium salt are more preferable.

Examples of the salt derived from an organic base include salts with organic amines such as primary amine, secondary amine, tertiary amine, substituted amine of these (including naturally-derived substituted amine) and cyclic amine, basic amino acid, and basic ion exchange resin. Examples of the organic amine and basic amino acid include isopropylamine, diethylamine, triethylamine, trimethylamine, tripropylamine, ethylenediamine, N,N'-dibenzylethylenediamine, 2-diethylaminoethanol, 2-dimethylaminoethanol, morpholine, N-ethyl-morpholine, piperazine, piperidine, N-ethylpiperidine, betaine, caffeine, choline, glucamine, glucosamine, histidine, hydrabamine, methylglucamine, lysine, arginine, polyamine resin, procaine, purine, and theobromine.

[Production Route of the Present Invention]

The production route of the present invention is summarized in the following Scheme 1. Hereinafter, the embodiments of the present invention are explained in detail for each step of Scheme 1. In the embodiments of the present invention, each step may be independently carried out, or some or all of them may be continuously carried out. When plural steps are continuously carried out, the reaction of each step may be stopped and then the next step may be performed, or the next step may be performed without stopping the previous reaction. Alternatively, purification may be performed after completion of a step and then the next step may be performed, or the next step may be performed without purification. Whether these steps are to be carried out or not can be optionally determined. The reactions of plural steps may be performed in the same reaction vessel or in different reaction vessels.

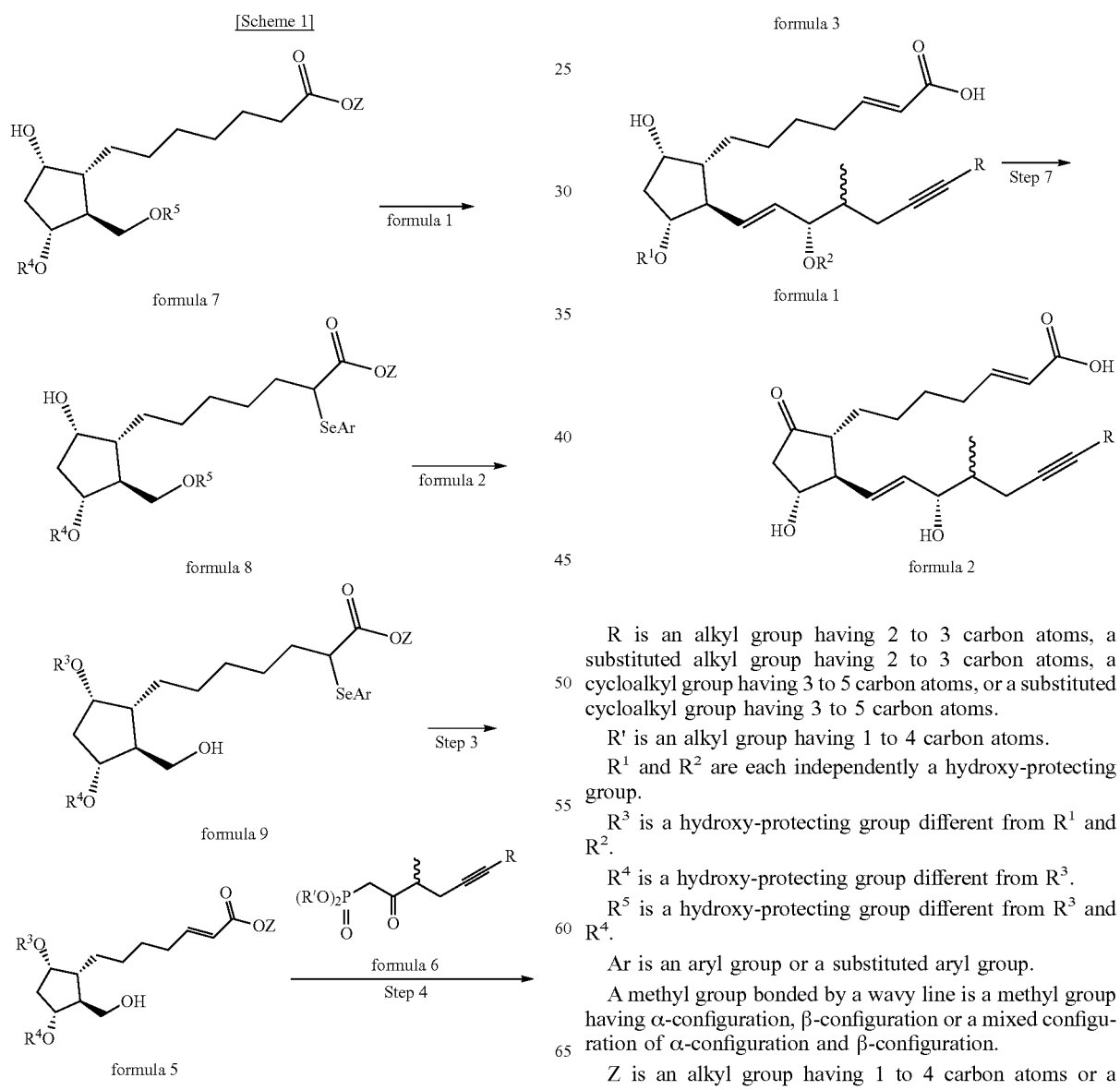

R is an alkyl group having 2 to 3 carbon atoms, a substituted alkyl group having 2 to 3 carbon atoms, a cycloalkyl group having 3 to 5 carbon atoms, or a substituted cycloalkyl group having 3 to 5 carbon atoms.

R' is an alkyl group having 1 to 4 carbon atoms.

$R^1$ and $R^2$ are each independently a hydroxy-protecting group.

$R^3$ is a hydroxy-protecting group different from $R^1$ and $R^2$.

$R^4$ is a hydroxy-protecting group different from $R^3$.

$R^5$ is a hydroxy-protecting group different from $R^3$ and $R^4$.

Ar is an aryl group or a substituted aryl group.

A methyl group bonded by a wavy line is a methyl group having α-configuration, β-configuration or a mixed configuration of α-configuration and β-configuration.

Z is an alkyl group having 1 to 4 carbon atoms or a substituted alkyl group having 1 to 4 carbon atoms.

[Production Step of compound (7)→Compound (8) (Step 1)]

Compound (8) can be produced by arylselenylating compound (7). In the following, a step of converting compound (7) to compound (8) by arylselenylation is referred to as Step 1.

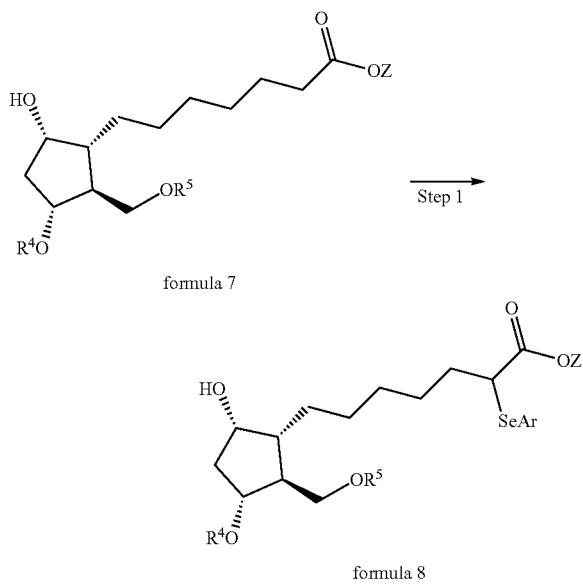

formula 7 formula 8

In compound (7), $R^4$ and $R^5$ are hydroxy-protecting groups different from each other, preferably, $R^4$ is a group that can be removed by adding an acid, and $R^5$ is a group that can be removed with a fluoride ion. Among them, $R^4$ is more preferably an alkoxyalkyl group such as methoxymethyl group, benzyloxymethyl group, tert-butoxymethyl group, 2-methoxyethoxymethyl group, 1-ethoxyethyl group, 1-methyl-1-methoxyethyl group or the like; a monovalent group having a cyclic ether structure such as 2-tetrahydropyranyl group, tetrahydrofuranyl group or the like, and $R^5$ is more preferably a tri-organosilyl group such as tert-butyldimethylsilyl group, tert-butyldiphenylsilyl group, trimethylsilyl group, triethylsilyl group, triphenylsilyl group, triisopropylsilyl group or the like.

Z is an alkyl group having 1 to 4 carbon atoms or a substituted alkyl group having 1 to 4 carbon atoms, preferably, a methyl group or an ethyl group.

Compound (7) wherein $R^4$ is a 2-tetrahydropyranyl group (hereinafter to be referred to as "THP"), $R^5$ is a tert-butyldimethylsilyl group (hereinafter to be referred to as "TBS"), and Z is methyl is most preferable.

When compound (7) is produced by a known method (e.g., the method described in JP-A-52-27753) or a method analogous thereto, it may be subjected to a reaction workup and then used as a starting compound of Step 1, or further purified and used as a highly pure compound. When compound (7) may be decomposed by the influence of water, air, heat and the like, it is preferably used for the reaction of Step 1 without undergoing the purification step.

In compound (8), $R^4$, $R^5$ and Z are as defined above.

Ar is an aryl group or a substituted aryl group, preferably an aryl group, or an aryl group having a halogen atom, an alkyl group having 1 to 8 carbon atoms, an alkoxy group having 1 to 8 carbon atoms or an alkylenedioxy group having 1 to 3 carbon atoms, more preferably a phenyl group or a phenyl group having a halogen atom, an alkyl group having 1 to 8 carbon atoms or an alkoxy group having 1 to 8 carbon atoms (e.g., 2-methylphenyl group, 3-methylphenyl group, 4-methylphenyl group, 2,4-di-tert-butylphenyl group, 4-methoxyphenyl group, 4-chlorophenyl group etc.), further preferably a phenyl group.

As the selenylation agent to be used in the arylselenylation in Step 1 is not particularly limited. For example, diphenyl diselenide (PhSeSePh), phenylselenyl halide (PhSeX, X=Br, Cl, I) and the like are easily commercially available products (e.g., manufactured by Sigma-Aldrich Ltd. etc.) and can be preferably used.

The amount of the selenylation agent to be used is preferably 1.0-5.0 mol, more preferably 1.2-4.0 mol, and further preferably 1.5-3.5 mol, per 1 mol of compound (7).

In Step 1, the reaction is performed in the presence of a base to initially generate an, enolate anion at the α-position of the ester group of compound (7). Examples of the base include alkali metal salts such as n-butyllithium, sec-butyllithium, lithium diisopropylamide, lithium hexamethyldisilazide, potassium hexamethyldisilazide and the like, and the like. As the base, n-butyllithium or lithium diisopropylamide is preferable, and lithium diisopropylamide is more preferable.

The amount of the base to be used is preferably 1.0-8.0 mol, more preferably 1.5-6.0 mol, further preferably 2.0-4.0 mol, per 1 mol of compound (7).

The reaction of Step 1 is performed in the presence of a solvent. The solvent is preferably selected from the solvents inert to the reaction, and is appropriately selected according to the reaction temperature, substrate solubility and the like. Examples of the solvent include ethers such as diethyl ether, tetrahydrofuran (hereinafter to be referred to as "THF"), dioxane and the like; aromatic hydrocarbon compounds such as benzene, toluene, xylene, mesitylene and the like; aliphatic hydrocarbon compounds such as hexane, heptane, octane, cyclohexane and the like. Only one kind of solvent may be used or two or more kinds thereof may be used in combination. In view of the reaction yield, the solvent to be used is preferably ether, more preferably diethyl ether or THF, and further preferably THF.

The amount of the solvent to be used is not particularly limited, and it is preferably 2- to 100-fold amount, more preferably 10- to 40-fold amount, based on the mass of compound (7).

The reaction temperature in Step 1 is preferably appropriately adjusted with the lower limit of about −80° C. and the boiling point of the solvent as the upper limit. In view of the reaction rate and reaction efficiency, for example, it is preferable to generate an enolate anion at a low temperature of −78 to 0° C., add a selenylation agent, and perform the reaction by maintaining at around −78° C. The temperature at which an enolate anion is generated is more preferably −78 to −40° C., further preferably −78° C. The reaction time is appropriately determined according to the amount and kind of the substrate and solvent, reaction temperature and the like. In view of the reaction rate and reaction efficiency, 5 min-24 hr is preferable, 10 min-6 hr is more preferable, and 30 min-2 hr is further preferable. The reaction atmosphere is appropriately selected according to the kind of the base to be used and the like. To prevent decomposition of the enolate anion of compound (7), an inert gas atmosphere of nitrogen, argon or the like is preferable.

A crude reaction product obtained by arylselenylation of compound (7) may be directly used for the next reaction, or compound (8) may be isolated and purified from the crude reaction product to remove by-products contained in the crude reaction product. As a method for isolation and purification, the methods known or well-known to those of ordinary skill in the art, for example, solvent extraction, distillation, sublimation, crystallization, silica gel column chromatography, preparative thin layer chromatography, preparative liquid chromatography, solvent washing and the like can be adopted.

[Production Step of Compound (8)→Compound (9) (Step 2)]

Compound (9) can be produced by protecting a hydroxy group of compound (8), and thereafter removing $R^5$. In the following, a step of converting compound (8) to compound (9) by protecting a hydroxy group of compound (8), and thereafter removing $R^5$ is referred to as Step 2.

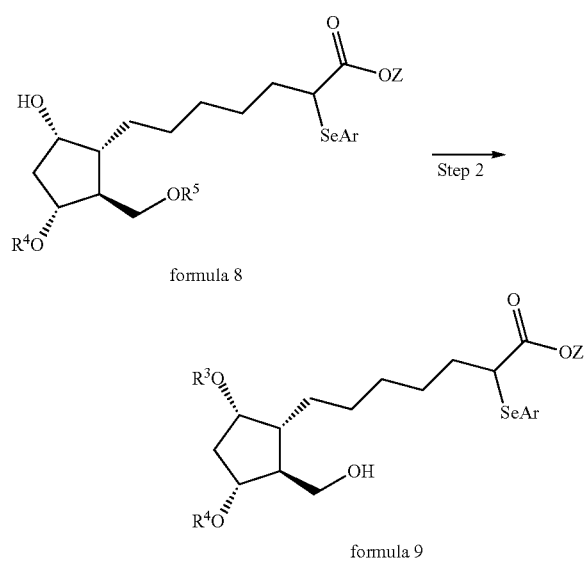

formula 8 formula 9

In compound (8), $R^4$, $R^5$, Z and Ar are as defined above. Compound (8) wherein $R^4$ is THP, $R^5$ is TBS, Z is a methyl group, and Ar is a phenyl group is most preferable.

In compound (9), $R^4$, Z and Ar are as defined above.

$R^3$ is a hydroxy-protecting group different from $R^4$ and $R^5$, preferably, $R^3$ is a group that can be removed under basic conditions. As $R^3$, an acyl group is more preferable. As the acyl group, an acetyl group, a trifluoroacetyl group, a propionyl group, a pivaloyl group, or a benzoyl group is preferable, and an acetyl group is more preferable.

The step of protecting a hydroxy group in Step 2 can be easily performed by the method described in "Protective Groups in Organic Synthesis) (T. W. Greene et. al., John Wiley&Sons, inc., 2007)" and the like.

Specifically, for example, when $R^3$ is an acyl group, the hydroxy group can be protected by an acyl group by a reaction of the hydroxyl group with acyl halide or the corresponding acid anhydride. The reaction may be performed in the presence of a base as necessary.

The acylating agent (protective agent) for the hydroxy group is not particularly limited and, for example, an acylating agent such as acetic anhydride, acetyl chloride, pivaloyl chloride, benzoyl chloride or the like can be preferably used. Acetic anhydride is preferably used since the reaction conditions are mild.

The amount of the acylating agent to be used is preferably 1.0-5.0 mol, more preferably 1.0-4.0 mol, further preferably 1.2-3.0 mol, per 1 mol of compound (8). In addition, an excess amount of an acylating agent can also be used as a reactant and solvent.

When an acylating agent is used as a reactant and solvent, the amount of the base to be used is preferably 3.0-30 mol, more preferably 4.0-20 mol, and further preferably 5.0-15 mol, per 1 mol of compound (8).

The step of protecting the hydroxy group is performed with or without solvent. The solvent is preferably selected from the solvents inert to the reaction, and is appropriately selected according to the reaction temperature, substrate solubility and the like. Examples thereof include ethers such as diethyl ether, THF, dioxane and the like; aromatic hydrocarbon compounds such as benzene, toluene, xylene, mesitylene and the like; aliphatic hydrocarbon compounds such as hexane, heptane, octane, cyclohexane, petroleum ether and the like; and halogenated hydrocarbon compounds such as chloroform, dichloromethane and the like. Only one kind of solvent may be used or two or more kinds thereof may be used in combination. In view of the reaction yield, the solvent to be used is preferably aromatic hydrocarbon compound, ether or halogenated hydrocarbon compound, more preferably diethyl ether, benzene, chloroform, petroleum ether or the like.

The base to be used in the reaction is not particularly limited. For example, organic bases such as triethylamine, N,N-diisopropylethylamine, N-methylmorpholine, pyridine, 2,6-lutidine, collidine, 4-dimethylaminopyridine and the like; and inorganic bases such as sodium carbonate, sodium hydrogen carbonate, potassium carbonate, potassium hydrogen carbonate, cesium carbonate and the like can be mentioned. Only one kind of the above-mentioned base may be used or two or more kinds thereof may be used in combination. Among these, pyridine or 4-dimethylaminopyridine is preferably used.

The amount of the base to be used is preferably 0.05-10 mol, more preferably 1.0-5.0 mol, and further preferably 1.2-2.0 mol, per 1 mol of compound (8). It is also possible to use an excess amount of a base as a reactant and solvent. When an excess amount of a base is used as a reactant and solvent, the amount of the base to be used is 3-50 mol, preferably 4-40 mol, more preferably 5-30 mol, per 1 mol of compound (8).

The reaction conditions such as reaction temperature, reaction time and the like vary depending on the reaction reagent, reaction solvent and the like to be used. Typically, the reaction temperature is −30 to 150° C., preferably −20 to 120° C. The reaction time is 30 min-20 hr.

The removal of $R^5$ in Step 2 can be easily performed under reaction conditions free from removal of $R^3$ or $R^4$ and by a deprotection method similar to those mentioned above.

Specifically, for example, when $R^5$ is a tri-organosilyl group, $R^5$ can be easily removed by the below-mentioned reaction with a deprotecting agent.

The deprotecting agent is not particularly limited as long as it is a compound that generates a fluoride ion. When $R^5$ is a tri-organosilyl group (e.g., TBS), for example, tetrabutylammonium fluoride can be preferably used.

The amount of the deprotecting agent to be used is preferably 1.0-5.0 mol, more preferably 1.1-3.0 mol, and further preferably 1.2-2.0 mol, per 1 mol of compound (8).

The reaction is performed in the presence of a solvent. The solvent is preferably selected from the solvents inert to the reaction, and is appropriately selected according to the reaction temperature, substrate solubility and the like. Examples thereof include ethers such as diethyl ether, THF, dioxane and the like; aromatic hydrocarbon compounds such as benzene, toluene, xylene, mesitylene and the like; aliphatic hydrocarbon compounds such as hexane, heptane, octane, cyclohexane and the like. Only one kind of solvent may be used or two or more kinds thereof may be used in combination. In view of the reaction yield, the solvent to be used is preferably ether, more preferably THF.

The amount of the solvent to be used is not particularly limited, and it is preferably 2- to 100-fold amount, more preferably 5- to 40-fold amount, based on the mass of compound (8).

The reaction conditions such as reaction temperature, reaction time and the like vary depending on the reaction reagent, reaction solvent and the like to be used. Typically, the reaction temperature is −30 to 150° C., preferably −20 to 120° C. The reaction time is 30 min-100 hr.

A crude reaction product obtained by the protection of the hydroxy group of compound (8) and removal of $R^5$ may be directly used for the next reaction. Compound (9) is preferably isolated and purified from the crude reaction product to remove by-products contained in the crude reaction product. As a method for isolation and purification, the methods described in the above-mentioned Step 1 can be adopted.

[Production Step of Compound (9)→Compound (5) (Step 3)]

Compound (5) can be produced by oxidatively eliminating an arylselenyl group of compound (9) to introduce a double bond.

In the following, a step of converting compound (9) to compound (5) by oxidatively eliminating an arylselenyl group of compound (9) to introduce a double bond is referred to as Step 3.

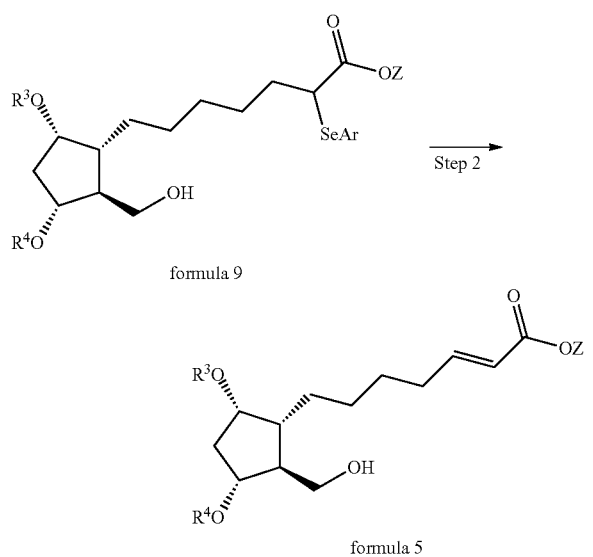

formula 9 formula 5

In compound (9), $R^3$, $R^4$, Z and Ar are as defined above. Compound (9) wherein $R^3$ is an acetyl group, $R^4$ is THP, Z is a methyl group, and Ar is a phenyl group is most preferable.

In compound (5), $R^3$, $R^4$ and Z are as defined above. Compound (5) wherein $R^3$ is an acetyl group, $R^4$ is THP, and Z is a methyl group is most preferable.

The step of oxidatively eliminating an arylselenyl group to introduce a double bond in Step 3 can be easily performed by a method known per se (e.g., the method described in "Jikken Kagaku Kouza 17 Synthesis of organic compound V oxidation reaction" p. 207-209 (MARUZEN)), or a method analogous thereto.

Specifically, for example, compound (5) can be produced by reacting compound (9) with an oxidant in the presence of a base.

The oxidant to be used in the reaction is not particularly limited. For example, hydrogen peroxide water, ozone, and m-chloroperbenzoic acid can be mentioned. Among these, hydrogen peroxide water or m-chloroperbenzoic acid is preferable, and hydrogen peroxide water (for example, 30% hydrogen peroxide water) is more preferable.

The amount of the oxidant to be used is preferably 1.0-10 mol, more preferably 1.0-6.0 mol, further preferably 2.0-5.0 mol, per 1 mol of compound (9).

The base to be used in the reaction is not particularly limited. For example, organic bases such as triethylamine, N,N-diisopropylethylamine, N-methylmorpholine, pyridine, 2,6-lutidine, collidine, 4-dimethylaminopyridine and the like; and inorganic bases such as sodium carbonate, sodium hydrogen carbonate, potassium carbonate, potassium hydrogen carbonate, cesium carbonate and the like can be mentioned. When hydrogen peroxide water is used as an oxidant, sodium carbonate, sodium hydrogen carbonate, potassium carbonate, potassium hydrogen carbonate, cesium carbonate, pyridine, or 4-dimethylaminopyridine is preferably used, and sodium hydrogen carbonate or pyridine is more preferably used.

The amount of the base to be used is preferably 1.0-5.0 mol, more preferably 1.1-4.0 mol, further preferably 1.2-3.5 mol, per 1 mol of compound (9).

The reaction of Step 3 is performed in the presence of a solvent. The solvent is preferably selected from the solvents inert to the reaction, and is appropriately selected according to the reaction temperature, substrate solubility and the like. Examples thereof include ethers such as diethyl ether, THF, dioxane and the like; esters such as ethyl acetate, methyl acetate, isopropyl acetate and the like; aromatic hydrocarbon compounds such as benzene, toluene, xylene, mesitylene and the like; aliphatic hydrocarbon compounds such as hexane, heptane, octane, cyclohexane and the like; and halogenated hydrocarbon compounds such as chloroform, dichloromethane and the like. Only one kind of solvent may be used or two or more kinds thereof may be used in combination. In view of the reaction yield, the solvent to be used is a mixed solvent of ether and ester, or a halogenated hydrocarbon compound, more preferably a mixed solvent of THF and ethyl acetate, or dichloromethane.

The amount of the solvent to be used is not particularly limited, and it is preferably 2- to 100-fold amount, more preferably 10- to 40-fold amount, based on the mass of compound (9).

The reaction conditions such as reaction temperature, reaction time and the like vary depending on the reaction reagent, reaction solvent and the like to be used. Typically, the reaction temperature is −30 to 150° C., preferably −10 to 40° C. The reaction time is 30 min-100 hr.

[Production Step of Compound (5)→Compound (4) (Step 4)]

Compound (4) can be produced by oxidizing a hydroxy group of compound (5) to convert same to the corresponding aldehyde, and performing a Horner-Wadsworth-Emmons reaction with compound (6). In the following, a step of oxidizing a hydroxy group of compound (5) to convert same to the corresponding aldehyde, and reacting same with compound (6) is referred to as Step 4.

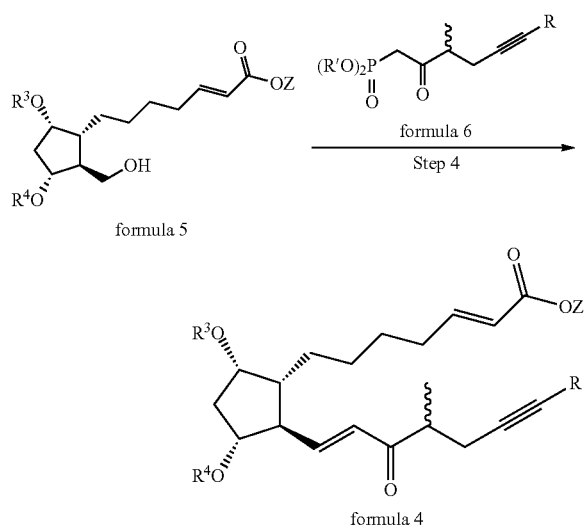

formula 5 formula 6 formula 4

In compound (5), $R^3$, $R^4$ and Z are as defined above.

Compound (5) wherein $R^3$ is an acetyl group, $R^4$ is THP, and Z is a methyl group is most preferable.

In compound (6), R is an alkyl group having 2 to 3 carbon atoms, a substituted alkyl group having 2 to 3 carbon atoms, a cycloalkyl group having 3 to 5 carbon atoms or a substituted cycloalkyl group having 3 to 5 carbon atoms, R' is an alkyl group having 1 to 4 carbon atoms, and a methyl group bonded by a wavy line is a methyl group having α-configuration, β-configuration or a mixed configuration of α-configuration and β-configuration.

Compound (6) wherein R is an ethyl group or a cyclopropyl group, and R' is a methyl group is most preferable.

In compound (4), R, $R^3$, $R^4$, a methyl group bonded by a m wavy line and Z are as defined above.

Compound (4) wherein R is an ethyl group or a cyclopropyl group, $R^3$ is an acetyl group, $R^4$ is THP, and Z is a methyl group is most preferable.

The oxidation step of a hydroxy group into aldehyde in Step 4 can be easily performed by a method known per se (e.g., the method described in "Jikken Kagaku Kouza 15 Synthesis of organic compound III aldehyde.ketone.quinone" p. 9-44 (MARUZEN)), or a method analogous thereto.

Specifically, for example, the corresponding aldehyde can be produced by reacting compound (5) with an oxidant.

The oxidant to be used in the reaction is not particularly limited. For example, dimethyl sulfoxide (hereinafter to be referred to as "DMSO")-oxalyl chloride (Swern oxidation), pyridine-sulfur trioxide ($SO_3$—Py)-DMSO (Parikh-Doering Oxidation), tetrapropylammonium perruthenate (TPAP), Dess-Martin reagent (1,1,1-triacetoxy-1,1-dihydro-1,2-benziodoxol-3(1H)-one), Jones reagent (concentrated sulfuric acid solution of anhydrous chromic acid), 2,2,6,6-tetramethylpiperidin-1-oxyl and iodobenzene diacetate, or 2-azaadamantine-N-oxyl and iodobenzene diacetate can be mentioned. Among these, pyridine-sulfur trioxide ($SO_3$—Py)-DMSO is preferable since reactions can be performed under mild reaction conditions and the work-up can also be performed conveniently.

When pyridine-sulfur trioxide ($SO_3$—Py)-DMSO is used, the oxidation reaction is performed in the presence of a base.

The amount of the oxidant to be used is preferably 1.0-10 mol, more preferably 1.1-6.0 mol, and further preferably 1.2-4.0 mol, per 1 mol of compound (5).

The base to be used in the reaction is not particularly limited and, for example, an organic base can be used. As the organic base, triethylamine, N,N-diisopropylethylamine, N-methylmorpholine, pyridine or 4-dimethylaminopyridine is preferably used, triethylamine or N,N-diisopropylethylamine is more preferable, and N,N-diisopropylethylamine is further preferable.

The amount of the base to be used is preferably 1.0-15 mol, more preferably 1.1-10 mol, and further preferably 1.2-8.0 mol, per 1 mol of compound (5).

The above-mentioned oxidation step in Step 4 is performed in the presence of a solvent. The solvent is preferably selected from the solvents inert to the reaction, and is appropriately selected according to the reaction temperature, substrate solubility and the like. Examples thereof include ethers such as diethyl ether, THF, dioxane and the like; esters such as ethyl acetate, methyl acetate, isopropyl acetate and the like; aromatic hydrocarbon compounds such as benzene, toluene, xylene, mesitylene and the like; aliphatic hydrocarbon compounds such as hexane, heptane, octane, cyclohexane and the like; and halogenated hydrocarbon compounds such as chloroform, dichloromethane and the like. Only one kind of solvent may be used or two or more kinds thereof may be used in combination. In view of the reaction yield, the solvent to be used is preferably ester, more preferably ethyl acetate.

The amount of the solvent to be used is not particularly limited, and it is preferably 2- to 100-fold amount, more preferably 10- to 40-fold amount, based on the mass of compound (5).

The reaction conditions such as reaction temperature, reaction time and the like vary depending on the reaction reagent, reaction solvent and the like to be used. Typically, the reaction temperature is −78 to 150° C., preferably −40 to 40° C. The reaction time is 20 min-100 hr.

The corresponding aldehyde of compound (5) can be converted to compound (4) by a Horner-Wadsworth-Emmons reaction with compound (6).

The Horner-Wadsworth-Emmons reaction step in Step 4 can be easily performed by a method known per se (e.g., the method described in JP-B-60-36422), or a method analogous thereto.

Specifically, compound (6) is dissolved in a solvent, and a base is reacted to generate an anion. Thereto is added the corresponding aldehyde of compound (5), and the mixture is reacted for a given time to produce compound (4).

The solvent of the Horner-Wadsworth-Emmons reaction step is preferably selected from the solvents inert to the reaction, and is appropriately selected according to the reaction temperature, substrate solubility and the like. Examples thereof include alcohols such as methanol, ethanol and the like; ethers such as THF, 1,2-dimethoxyethane and the like; sulfoxides such as DMSO and the like; and nitriles such as acetonitrile and the like. Only one kind of solvent may be used or two or more kinds thereof may be used in combination. In view of the reaction yield, the solvent to be used is preferably ether or nitrile, more preferably acetonitrile.

The amount of the solvent to be used is not particularly limited, and it is preferably 2- to 100-fold amount, more preferably 10- to 40-fold amount, based on the mass of compound (5).

The base to be used in the reaction is not particularly limited. For example, an alkali metal salt such as sodium hydride, sodium hexamethyldisilazide, sodium methoxide, potassium tert-butoxide or the like; or an organic base such as triethylamine, N,N-diisopropylethylamine, N-methylmorpholine, pyridine, 4-dimethylaminopyridine, diazabicycloundecene or the like is preferably used, more preferably triethylamine or N,N-diisopropylethylamine, further preferably N,N-diisopropylethylamine. When the hydroxy-protecting group is unstable under basic conditions, the above-mentioned organic base and lithium chloride are preferably used in combination. The amount of the base to be used is preferably 1.0-5.0 mol, more preferably 1.1-3.0 mol, and further preferably 1.2-2.0 mol, per 1 mol of compound (5).

The reaction conditions such as reaction temperature, reaction time and the like vary depending on the reaction reagent, reaction solvent and the like to be used. Typically, the reaction temperature is −78 to 150° C., preferably 10 to 40° C. The reaction time is 30 min-100 hr.

[Production Step of Compound (4)→Compound (3) (Step 5)]

Compound (3) can be produced by reducing a carbonyl group of compound (4), and removing $R^4$. In the following, a step of converting compound (4) to compound (3) by reducing the carbonyl group of compound (4), and removing $R^4$ is referred to as Step 5.

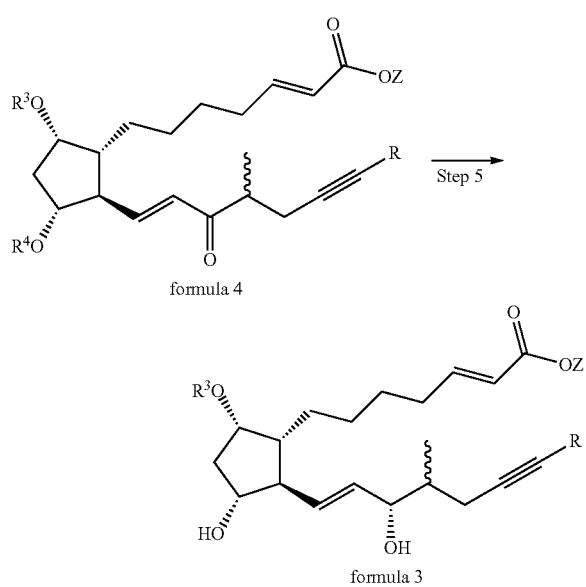

formula 4 formula 3

In compound (4), R, $R^3$, $R^4$, a methyl group bonded by a wavy line and Z are as defined above.

In compound (3), R, $R^3$, a methyl group bonded by a wavy line and Z are as defined above.

Compound (3) wherein R is an ethyl group or a cyclopropyl group, $R^3$ is an acetyl group, and Z is a methyl group is most preferable.

The reduction step of a carbonyl group to a hydroxy group in Step 5 can be easily performed by a method known per se (e.g., the methods described in "Jikken Kagaku Kouza 14, synthesis of organic compound II, alcohol.amine" p. 1-49 (MARUZEN) or "Jikken Kagaku Kouza 19, synthesis of organic compound VII, asymmetric synthesis.radical reaction" p. 90-112 (MARUZEN)), or a method analogous thereto. Specifically, a compound in which carbonyl group is reduced to hydroxy group (hereinafter to be referred to as "hydroxy form") can be produced by reacting compound (4) with a reducing agent.

The reducing agent to be used in the reaction is not particularly limited. Examples thereof include sodium borohydride-cerium chloride, sodium borohydride-calcium chloride, diisobutylaluminum hydride, lithium aluminum hydride, β-chlorodiisopinocampheylborane, lithium tri-sec-butylhydroborate, potassium tri-sec-butylhydroborate, and sodium tri-sec-butylhydroborate. When a stereo-selective reduction reaction is performed, Corey-Bakshi-Shibata (CBS) reduction in which asymmetric reduction of ketone is performed using a chiral oxazaborolidine catalyst and borane (e.g., diethylaniline borane, borane THF complex, dimethylsulfide borane) is most preferably used.

A commercially available product of CBS chiral oxazaborolidine catalyst can be directly used, or easily prepared by a method known per se (e.g., the method described in U.S. Pat. No. 7,586,015) or a method analogous thereto.

The amount of the reducing agent to be used is preferably 0.2-5.0 mol, more preferably 0.3-3.0 mol, and further preferably 0.5-2.0 mol, per 1 mol of compound (4).

The amount of the CBS chiral oxazaborolidine catalyst to be used is preferably 0.01-5.0 mol, more preferably 0.2-3.0 mol, and further preferably 1.0-2.0 mol, per 1 mol of compound (4).

The reduction reaction in Step 5 is performed in the presence of a solvent. The solvent is preferably selected from the solvents inert to the reaction, and is appropriately selected according to the reaction temperature, substrate solubility and the like. Examples thereof include alcohols such as methanol, ethanol and the like; ethers such as diethyl ether, THF, dioxane and the like; and aromatic hydrocarbon compounds such as benzene, toluene, xylene, mesitylene and the like. Only one kind of solvent may be used or two or more kinds thereof may be used in combination. As a solvent for a stereo-selective reduction reaction, an aromatic hydrocarbon compound is preferably used, and toluene is most preferably used.

The amount of the solvent to be used is not particularly limited, and it is preferably 2- to 100-fold amount, more preferably 5- to 40-fold amount, based on the mass of compound (4).

The reaction conditions such as reaction temperature, reaction time and the like vary depending on the reaction reagent, reaction solvent and the like to be used. Typically, the reaction temperature is −30 to 100° C., preferably −10 to 40° C. The reaction time is 20 min-100 hr.

Compound (4) can be converted to compound (3) by removing $R^4$ from the hydroxy form of compound (4).

The step of converting the compound in which a carbonyl group of compound (4) is reduced to a hydroxy group to compound (3) by removing $R^4$ in Step 5 can be easily performed under reaction conditions free from removal of $R^3$ and by the same deprotection method as mentioned above.

Specifically, for example, when $R^4$ is a monovalent group, which can be removed by adding an acid, having a cyclic ether structure such as an alkoxyalkyl group such as methoxymethyl group, benzyloxy methyl group, tert-butoxy methyl group, 2-methoxyethoxymethyl group, 1-ethoxyethyl group, 1-methyl-1-methoxyethyl group or the like; 2-tetrahydropyranyl group, tetrahydrofuranyl group or the like, the step can be performed by adding an acid as a deprotecting agent in the presence of a solvent.

The acid to be used as a deprotecting agent in the reaction is not particularly limited. For example, acetic acid, trifluoroacetic acid or hydrochloric acid can be mentioned, and it is preferably hydrochloric acid or acetic acid, more preferably hydrochloric acid. Hydrochloric acid is preferably used as 0.1N hydrochloric acid.

The amount of the acid to be used is 0.02-10 mol, preferably 0.05-5.0 mol, more preferably 0.1-4.0 mol, per 1 mol of the hydroxy form of compound (4). It is also possible to use an excess amount of an acid as a reactant and solvent. When an excess amount of an acid is used as a reactant and solvent, the amount of the acid to be used is 3.0-50 mol, preferably 4.0-30 mol, more preferably 5.0-20 mol, per 1 mol of the hydroxy form of compound (4).

The removal of $R^4$ in Step 5 is performed in the presence of a solvent. The solvent is preferably selected from the solvents inert to the reaction, and is appropriately selected according to the reaction temperature, substrate solubility and the like. Examples thereof include alcohols such as methanol, ethanol and the like; nitriles such as acetonitrile and the like; ethers such as diethyl ether, THF, dioxane and the like; aromatic hydrocarbon compounds such as benzene, toluene, xylene, mesitylene and the like; halogenated hydrocarbon solvents such as chloroform, dichloromethane and the like, and the like. Only one kind of solvent may be used or two or more kinds thereof may be used in combination. In view of the reaction yield, the solvent to be used is preferably ether, alcohol, nitrile or a mixed solvent of alcohol and nitrile, more preferably a mixed solvent of methanol and acetonitrile. As the mixed solvent of methanol and acetonitrile, a mixed solvent of methanol and acetonitrile at a volume ratio (methanol:acetonitrile) of about 1:2 is further preferable.

The amount of the solvent to be used is not particularly limited, and it is preferably 2- to 100-fold amount, more preferably 4- to 40-fold amount, based on the mass of the hydroxy form of compound (4).

The reaction conditions such as reaction temperature, reaction time and the like vary depending on the reaction reagent, reaction solvent and the like to be used. Typically, the reaction temperature is −10 to 100° C., preferably, 10 to 60° C., more preferably, 20 to 50° C. The reaction time is 20 min-48 hr.

A crude reaction product of compound (3) obtained in Step 5 may be directly used for the next reaction. Compound (3) may be isolated and purified from the crude reaction product to remove by-products contained in the crude reaction product. As a method for isolation and purification, the methods described in the above-mentioned Step 1 can be adopted.

[Production Step of Compound (3)→Compound (1) (Step 6)]

Compound (1) or a pharmaceutically acceptable salt thereof can be produced by protecting two hydroxy groups of compound (3) and subsequently removing $R^3$ and hydrolyzing a $CO_2Z$ group. In the following, a step of converting compound (3) to compound (1) or a pharmaceutically acceptable salt thereof by protecting the hydroxy groups of compound (3) and subsequently removing $R^3$ and hydrolyzing the $CO_2Z$ group is referred to as Step 6.

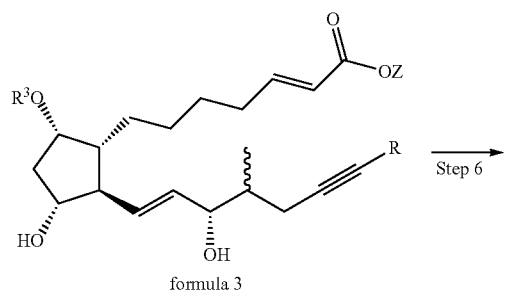

formula 3

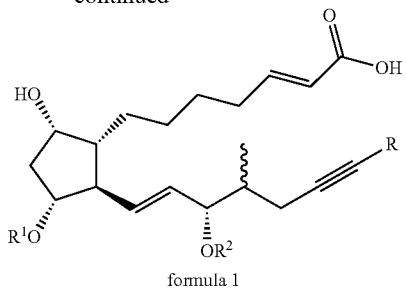

formula 1

In compound (3), R, $R^3$, a methyl group bonded by a wavy line and Z are as defined above.

In compound (1), R and a methyl group bonded by a wavy line are as defined above.

$R^1$ and $R^2$ are each independently a hydroxy-protecting group different from $R^3$. $R^1$ and $R^2$ are preferably monovalent groups, which can be removed by adding an acid, having a cyclic ether structure such as an alkoxyalkyl group such as methoxymethyl group, benzyloxymethyl group, tert-butoxymethyl group, 2-methoxyethoxymethyl group, 1-ethoxyethyl group, 1-methyl-1-methoxyethyl group or the like; 2-tetrahydropyranyl group, tetrahydrofuranyl group or the like, more preferably, $R^1$ and $R^2$ are both methoxymethyl groups or 2-tetrahydropyranyl groups.

Compound (1) wherein R is an ethyl group or a cyclopropyl group, and $R^1$ and $R^2$ are each THP is most preferable.

The step of protecting two hydroxy groups in Step 6 can be easily performed by the above-mentioned known protection method of hydroxyl group.

Specifically, for example, when $R^1$ and $R^2$ are THPs, the two hydroxy groups of compound (3) can be protected by THP by a reaction of compound (3) with 3,4-dihydro-2H-pyran in the presence of an acid catalyst.

The amount of 3,4-dihydro-2H-pyran to be used is preferably 2.0-6.0 mol, more preferably 2.4-4.0 mol, per 1 mol of compound (3).

The acid catalyst to be used in the reaction is not particularly limited and, for example, p-toluenesulfonic acid monohydrate, pyridinium p-toluenesulfonate, hydrochloric acid, and phosphoryl chloride can be mentioned. Among these, p-toluenesulfonic acid monohydrate is most preferable.

The amount of the acid catalyst to be used is preferably 0.0001-0.5 mol, more preferably 0.001-0.2 mol, and further preferably 0.005-0.1 mol, per 1 mol of compound (3).

The reaction is performed in the presence of a solvent. The solvent is preferably selected from the solvents inert to the reaction, and is appropriately selected according to the reaction temperature, substrate solubility and the like. Examples thereof include halogenated hydrocarbon compounds such as dichloromethane, chloroform, 1,2-dichloroethane and the like; and aromatic hydrocarbon compounds such as benzene, toluene, xylene, mesitylene and the like. Only one kind of solvent may be used or two or more kinds thereof may be used in combination. In view of the reaction yield, the solvent to be used is preferably a halogenated hydrocarbon compound such as dichloromethane, chloroform, 1,2-dichloroethane or the like, most preferably dichloromethane.

The amount of the solvent to be used is not particularly limited, and it is preferably 2- to 100-fold amount, more preferably 10- to 40-fold amount, based on the mass of compound (3).

The reaction conditions such as reaction temperature, reaction time and the like vary depending on the reaction reagent, reaction solvent and the like to be used. Typically, the reaction temperature is −30 to 100° C., preferably 0 to 40° C. The reaction time is 20 min-24 hr.

The compound in which a hydroxy group of compound (3) is protected (hereinafter to be referred to as "hydroxy group protected form") can be converted to compound (1) by removal of $R^3$ and hydrolysis of an ester group ($CO_2Z$ group).

The step of converting the hydroxy group protected form of compound (3) to compound (1) by removal of $R^3$ and hydrolysis of the $CO_2Z$ group in Step 6 can be easily performed by removal of $R^3$ and hydrolysis of the $CO_2Z$ group (removal of Z) under reaction conditions free from removal of $R^1$ or $R^2$ and by the above-mentioned known deprotection method.

When $R^3$ is a group such as acyl group that can be removed under basic conditions, the hydrolysis of the $CO_2Z$ group simultaneously proceeds, which is favorable since efficient conversion to compound (1) can be achieved.

The base to be used for the removal of $R^3$ and hydrolysis of the $CO_2Z$ group in this step is not particularly limited. For example, lithium hydroxide, sodium hydroxide, potassium hydroxide, cesium hydroxide, barium hydroxide, calcium hydroxide, potassium tert-butoxide, sodium tert-butoxide, or potassium carbonate can be mentioned. Sodium hydroxide, potassium hydroxide or lithium hydroxide is preferable, since it is effective for the acceleration of the reaction and the improvement of the yield, and lithium hydroxide (e.g., lithium hydroxide monohydrate) is more preferable.

The amount of the above-mentioned base to be used is 1.0-30 mol, preferably 1.2-15 mol, per 1 mol of the hydroxy group protected form of compound (3).

The removal of $R^3$ and hydrolysis of $CO_2Z$ group in Step 6 are performed in the presence of a solvent. The solvent is preferably selected from the solvents inert to the reaction, and is appropriately selected according to the reaction temperature, substrate solubility and the like. Examples thereof include alcohols such as methanol, ethanol and the like; ethers such as diethyl ether, THF, dioxane and the like; and aromatic hydrocarbon compounds such as benzene, toluene, xylene, mesitylene and the like. Only one kind of solvent may be used or two or more kinds thereof may be used in combination.

In view of the reaction yield, the solvent to be used is preferably ether, more preferably THF.

The amount of the solvent to be used is not particularly limited, and it is preferably 2- to 100-fold amount, more preferably 4- to 40-fold amount, based on the mass of the hydroxy group protected form of compound (3).

The reaction conditions such as reaction temperature, reaction time and the like vary depending on the reaction reagent, reaction solvent and the like to be used. Typically, the reaction temperature is −10 to 100° C., preferably, 10 to 60° C., more preferably, 20 to 50° C. The reaction time is 20 min-72 hr.

A crude reaction product of compound (1) obtained in Step 6 may be directly used for the next reaction. Compound (1) may be isolated and purified from the crude reaction product to remove by-products contained in the crude reaction product. As a method for isolation and purification, the methods described in the above-mentioned Step 1 can be adopted.

[Production Step of Compound (1)→Compound (2) (Step 7)]

Compound (2) or a pharmaceutically acceptable salt thereof can be produced by oxidizing a hydroxy group of compound (1) or a pharmaceutically acceptable salt thereof, and then removing $R^1$ and $R^2$. In the following, a step of converting compound (1) or a pharmaceutically acceptable salt thereof to compound (2) or a pharmaceutically acceptable salt thereof by oxidizing a hydroxy group of compound (1) or a pharmaceutically acceptable salt thereof, and then removing $R^1$ and $R^2$ is referred to as Step 7.

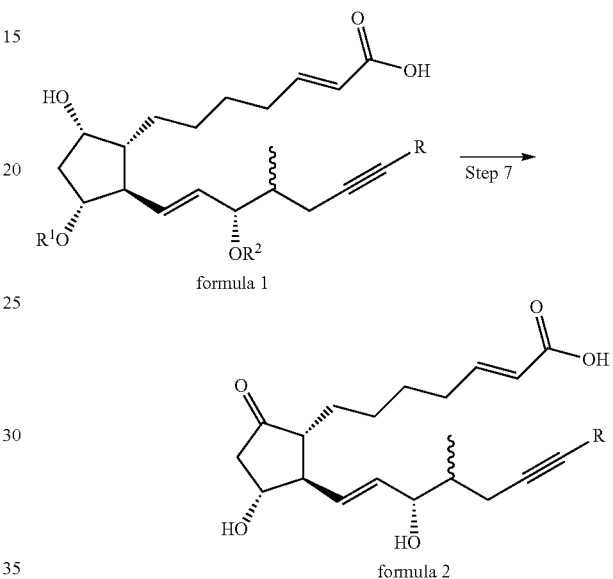

In compound (1), R, $R^1$, $R^2$ and a methyl group bonded by a wavy line are as defined above.

In compound (2), R and a methyl group bonded by a wavy line are as defined above.

Compound (2) wherein R is an ethyl group or a cyclopropyl group is most preferable.

The step of oxidizing a hydroxy group of compound (1) in Step 7 can be easily performed by a method known per se (the method described in "Jikken Kagaku Kouza 15 Synthesis of organic compound III aldehyde. ketone.quinone" p. 163-211 (MARUZEN)), or a method analogous thereto.

Specifically, for example, a compound in which the hydroxy group of compound (1) is converted to a carbonyl group (hereinafter to be referred to as "carbonyl form") can be produced by reacting compound (1) with an oxidant.

The oxidant to be used in the reaction is not particularly limited. For example, DMSO-oxalyl chloride (Swern oxidation), pyridine-sulfur trioxide ($SO_3$—Py)-DMSO (Parikh-Doering Oxidation), tetrapropylammonium perruthenate (TPAP), Dess-Martin reagent (1,1,1-triacetoxy-1,1-dihydro-1,2-benziodoxol-3(1H)-one), Jones reagent (concentrated sulfuric acid solution of anhydrous chromic acid), 2,2,6,6-tetramethylpiperidin-1-oxyl and iodobenzene diacetate, or 2-aza adamantine-N-oxyl and iodobenzene diacetate can be mentioned. Among these, Dess-Martin reagent is preferable in view of reaction yield and convenience of experiment operations.

The amount of the oxidant to be used is preferably 1.0-5.0 mol, more preferably 1.1-3.0 mol, and further preferably 1.2-1.5 mol, per 1 mol of compound (1).

The reaction is performed in the presence of a solvent. The solvent is preferably selected from the solvents inert to the reaction, and is appropriately selected according to the reaction temperature, substrate solubility and the like. Examples thereof include halogenated hydrocarbon compounds such as dichloromethane, chloroform, 1,2-dichloroethane and the like; and aromatic hydrocarbon compounds such as benzene, toluene, xylene, mesitylene and the like. Only one kind of solvent may be used or two or more kinds thereof may be used in combination. In view of the reaction yield, the solvent to be used is preferably a halogenated hydrocarbon compound such as dichloromethane, chloroform, 1,2-dichloroethane or the like, most preferably dichloromethane.

The amount of the solvent to be used is not particularly limited, and it is preferably 2- to 100-fold amount, more preferably 10- to 40-fold amount, based on the mass of compound (1).

The reaction conditions such as reaction temperature, reaction time and the like vary depending on the reaction reagent, reaction solvent and the like to be used. Typically, the reaction temperature is 0 to 100° C., preferably 10 to 40° C. The reaction time is 10 min-24 hr.

Compound (2) can be produced by removing $R^1$ and $R^2$ from the carbonyl form of compound (1).

The step of converting to compound (2) by removing $R^1$ and $R^2$ from the carbonyl form of compound (1) in Step 7 can be easily performed by the above-mentioned known deprotection method.

Specifically, for example, when $R^1$ and $R^2$ are monovalent groups (preferably, 2-tetrahydropyranyl groups) that can be removed by the addition of an acid as mentioned above, the compound can be efficiently converted to compound (2) by adding an acid.

The acid to be used as a deprotecting agent in this step is, for example, acetic acid, trifluoroacetic acid, hydrochloric acid or the like, preferably acetic acid or hydrochloric acid, more preferably hydrochloric acid. Hydrochloric acid is preferably used as 0.1N hydrochloric acid.

The amount of the acid to be used is 0.02-10 mol, preferably 0.05-5.0 mol, more preferably 0.1-4.0 mol, per 1 mol of the carbonyl form of compound (1). It is also possible to use an excess amount of an acid as a solvent. When an excess amount of an acid is used as a solvent, the amount of the acid is 3.0-50 mol, preferably 4.0-30 mol, more preferably 5.0-20 mol, per 1 mol of the carbonyl form of compound (1).

The removal of $R^1$ and $R^2$ in this step is performed in the presence of a solvent. The solvent is preferably selected from the solvents inert to the reaction, and is appropriately selected according to the reaction temperature, substrate solubility and the like. Examples thereof include alcohols such as methanol, ethanol and the like; nitriles such as acetonitrile and the like; ethers such as diethyl ether, THF, dioxane and the like; aromatic hydrocarbon compounds such as benzene, toluene, xylene, mesitylene and the like; halogenated hydrocarbon solvents such as chloroform, dichloromethane and the like, and the like. Only one kind of solvent may be used or two or more kinds thereof may be used in combination. In view of the reaction yield, the solvent to be used is preferably ether, alcohol, nitrile, or alcohol and nitrile, more preferably a mixed solvent of methanol and acetonitrile. As the mixed solvent of methanol and acetonitrile, a mixed solvent of methanol and acetonitrile at a volume ratio (methanol:acetonitrile) of about 1:2 is further preferable.

The amount of the solvent to be used is not particularly limited, and it is preferably to 100-fold amount, more preferably 4- to 40-fold amount, based on the mass of the carbonyl form of compound (1).

The reaction conditions such as reaction temperature, reaction time and the like vary depending on the reaction reagent, reaction solvent and the like to be used. Typically, the reaction temperature is −10 to 100° C., preferably 10 to 60° C., more preferably 20° C.-50° C. The reaction time is 20 min-48 hr.

The compound represented by the formula 2 is useful as an antiplatelet agent or a blood flow improving agent. A compound represented by the formula 2 or a pharmaceutically acceptable salt thereof can be produced in a good yield by the production method of the present invention.

According to the production method of the present invention, the purity of the target product is easily improved, and a compound represented by the formula 2 or a pharmaceutically acceptable salt thereof can be produced conveniently with a high purity by introducing a double bond into the 2-position of prostaglandin in the initial stage of synthesis, as compared to the introduction in the final stage of the synthesis. Particularly, the content of analogues that causes problems in the double bond introduction reaction is easily controlled, and a highly pure compound necessary for pharmaceutical products can be produced stably and efficiently. As specific characteristics of the production method of the present invention, the following can be mentioned.

(A) By introducing a double bond into the 2-position of prostaglandin at the initial stage of synthesis, the purity of the target compound in each step is improved as compared to introduction of the double bond at the final stage of synthesis. As a result, compound (2) or a pharmaceutically acceptable salt thereof can be produced conveniently with a high purity. In particular, the production method of the present invention can easily control the content of analogues, such as geometrical isomers (Z form), dihydro forms in which the double bond portion is a single bond and the like, that cause problems in general double bond introduction reactions. Therefore, highly pure compounds necessary for pharmaceutical products can be produced stably and efficiently.

(B) A multi-step reaction can be efficiently performed by properly using a hydroxy-protecting group.

(C) A highly stereo-selective reduction can be performed using the Corey-Bakshi-Shibata (CBS) reduction in Step 5.

(D) Compound (3) and compound (4) are important intermediates in the present production method, a highly efficient production method can be provided by going through these compounds.

EXAMPLE

The present invention is explained in detail in the following by referring to Examples; however, the present invention is not limited thereto.

% means mol % for yield and mass % for others unless particularly indicated. The room temperature refers to a temperature of 15-30° C. unless particularly indicated. The following $^1$H-NMR values were measured at a resolution of 400 MHz.

Reference Example 1

Production of methyl 7-((1R,2R,3R,5S)-5-hydroxy-2-(((tert-butyldimethylsilyl)oxy)methyl)-3-((tetrahydro-2H-pyran-2-yl)oxy)cyclopentyl)heptanoate (Compound (7a))

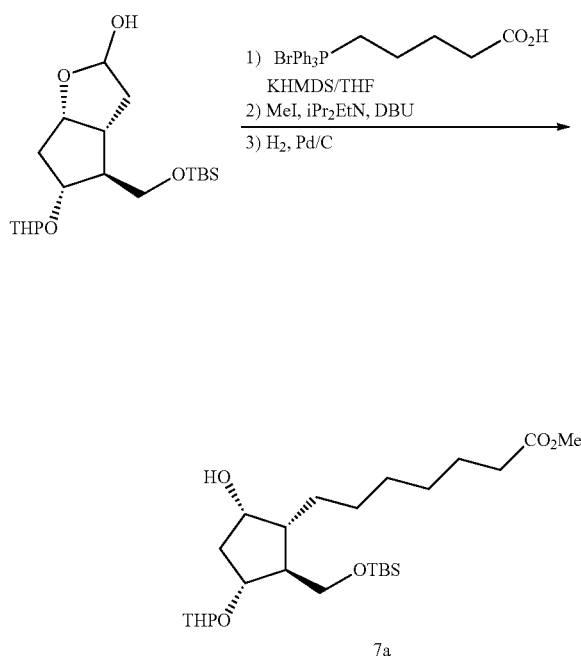

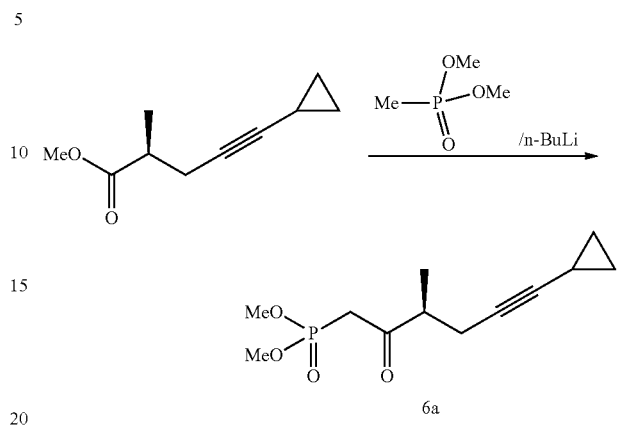

To a suspension of 4-(carboxybutyl)triphenylphosphonium bromide (107 g) in THF (657 mL) was added 1 M potassium bis(trimethylsilyl)amide (KHMDS) (483 mL) and the mixture was stirred for 1 hr and cooled to −78° C. Then, a solution of (3aR,4S,5R,6aS)-4-(((tert-butyldimethylsilyl)oxy)methyl)hexahydro-5-((tetrahydro-2H-pyran-2-yl)oxy)-2H-cyclopenta[b]furan-2-ol (30 g) in THF (377 mL) was added thereto and the mixture was stirred at the same temperature for 30 min. The mixture was heated to room temperature and stirred overnight to give a mixture. Water was added to the mixture and the mixture was extracted with tert-butylmethylether, acidified with disodium hydrogen citrate and extracted with ethyl acetate. The obtained organic layer was dried over anhydrous sodium sulfate, and concentrated under reduced pressure. Acetone (1440 mL) was added thereto, N,N-diisopropylethylamine (iPr$_2$EtN) (58.8 mL), methyl iodide (MeI) (22.1 mL) and 1,8-diazabicyclo[5.4.0]undec-7-ene (DBU) (68.6 mL) were added at 0° C., and the mixture was stirred at room temperature for 3.5 hr. Then, saturated aqueous sodium hydrogen carbonate was added and the mixture was extracted with ethyl acetate and concentrated under reduced pressure. The residue was purified by silica gel column chromatography to give a viscous oil (26.4 g). To the oil (26.4 g) was added ethyl acetate (1494 mL), and the mixture was stirred under a hydrogen atmosphere for 40 min using 5% Pd/C (9.9 g) as a catalyst. The catalyst was filtered off, and the filtrate was concentrated under reduced pressure. The residue was purified by silica gel column chromatography using a mobile phase in which a gradient was applied from a mixed solution of hexane:ethyl acetate=3:1 (vol) to a mixed solution of hexane:ethyl acetate=1:3 (vol) to give compound (7a) (20.2 g).

$^1$H NMR (300 MHz, CDCl$_3$) δ4.68 (m, 1H), 4.22-4.19 (m, 1H), 4.15-4.04 (m, 1H), 3.88-3.73 (m, 2H), 3.66 (s, 3H), 3.60-3.38 (m, 2H), 2.55-2.25 (m, 1H), 2.24 (t, J=7.5 Hz, 2H), 1.95-1.15 (m, 21H), 0.87(d, J=3.0 Hz, 9H), 0.03(d, J=3.0 Hz, 6H)

Reference Example 2

Production of dimethyl (S)-(+)-(6-cyclopropyl-3-methyl-2-oxohex-5-yn-1-yl)phosphonate (Compound (6a))

THF (76.1 mL) was added to dimethyl methylphosphonate (13.3 g), and 2.65 M n-butyllithium (39.5 mL) was added dropwise thereto at −78° C. The reaction mixture was stirred at −78° C. for 1 hr, a solution of methyl (S)-5-cyclopropyl-2-methylpent-4-ynoate (7.50 g) in THF (32.6 mL) was added thereto, and the mixture was stirred at the same temperature for 4 hr to give a mixture. To the mixture was added an aqueous ammonium chloride solution, and the mixture was extracted with ethyl acetate, dried over anhydrous magnesium sulfate, and concentrated under reduced pressure. The residue was purified by silica gel column chromatography using a mobile phase in which a gradient was applied from a mixed solution of hexane:ethyl acetate =3:1 (vol) to hexane to give compound (6a) (7.10 g). yield 61%.

$^1$H NMR (400 MHz, CDCl$_3$) δ3.81 (s, 3H), 3.78 (s, 3H), 3.20 (ddd, J=14.4, 22.8, 28.4 Hz, 2H), 2.91 (q, J=6.8 Hz, 1H), 2.33 (dddd, J=2.0, 6.8, 16.8, 44.4 Hz, 2H), 1.18 (d, J=7.2 Hz, 3H), 1.18 (m, 1H), 0.71 (m, 2H), 0.60 (m, 2H).

Example 1

Production of methyl 7-((1R,2R,3R,5S)-5-hydroxy-2-(((tert-butyldimethylsilyl)oxy)methyl)-3-((tetrahydro-2H-pyran-2-yl)oxy)cyclopentyl)2-phenylselenoheptanoate (Compound (8a)) (Step 1)

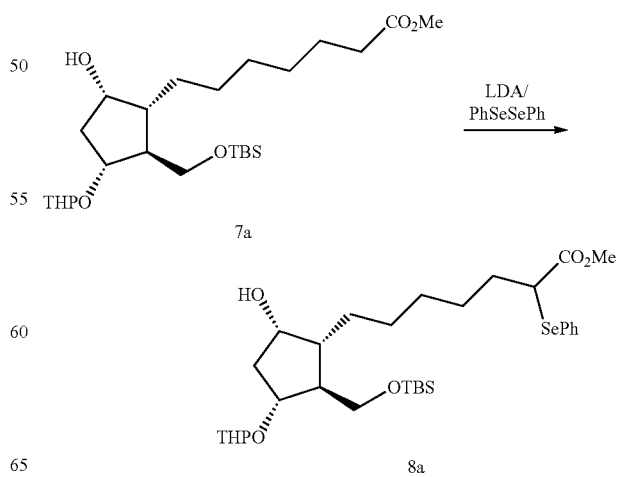

15.0 g of compound (7a) produced in Reference Example 1 was dissolved in 350 mL of THF, a solution (104 mL) of 1.12 M lithium diisopropylamide (LDA) in THF was added thereto at −78° C., and the mixture was stirred at the same temperature for 30 min. A solution of diphenyl diselenide (PhSeSePh) (24.8 g) in THF (53 mL) was added dropwise at −78° C., and the mixture was stirred at the same temperature for about 2 hr to give a mixture. The mixture was diluted with ethyl acetate, partitioned by adding saturated aqueous ammonium chloride solution, and the aqueous layer was extracted with ethyl acetate. The obtained organic layers were combined, washed with saturated brine, dried over anhydrous sodium sulfate, and concentrated under reduced pressure to give compound (8a) as a crude product (19.9 g).

Example 2

Production of methyl (2E)-7-((1R,2R,3R,5S)-5-acetoxy-2-hydroxymethyl-3-((tetrahydro-2H-pyran-2-yl)oxy)cyclopentyl)2-phenylselenoheptanoate (Compound (9a)) (Step 2)

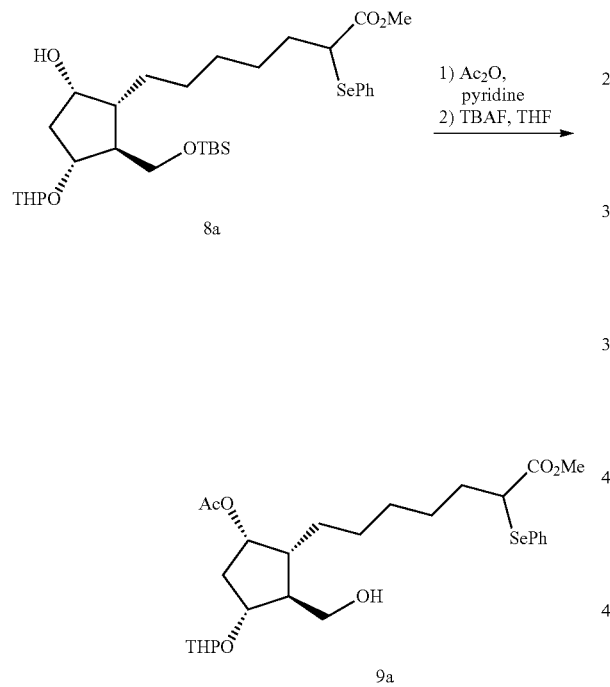

To the crude product (19.9 g) of compound (8a) obtained in Example 1 were added pyridine (33.3 mL), acetic anhydride ($Ac_2O$) (33.3 mL), and 4-dimethylaminopyridine (387 mg) and the mixture was stirred at room temperature for 1 hr. Water was added thereto, and the mixture was extracted with a mixed solvent of hexane and ethyl acetate. The obtained organic layer was dried over anhydrous sodium sulfate, concentrated under reduced pressure, THF (176 mL) was added and the mixture was ice-cooled. 1 M tetrabutylammonium fluoride (TBAF) (63.5 mL) was added, and the mixture was stirred at room temperature for 3 hr to give a mixture. The mixture was concentrated under reduced pressure and purified by silica gel column chromatography using a mobile phase in which a gradient was applied from a mixed solution of hexane:ethyl acetate=3:1 (vol) to a mixed solution of hexane:ethyl acetate=1:3 (vol) to give compound (9a) (14.1 g) as an oil. The content of the geometrical isomer with a double bond moiety at the 2-position (Z form) and the content of the dihydro form having a single bond at the double bond moiety were not more than 0.1%.

Example 3

Production of methyl (2E)-7-((1R,2R,3R,5S)-5-acetoxy-2-hydroxymethyl-3-((tetrahydro-2H-pyran-2-yl)oxy)cyclopentyl)hept-2-enoate (Compound (5a)) (Step 3)

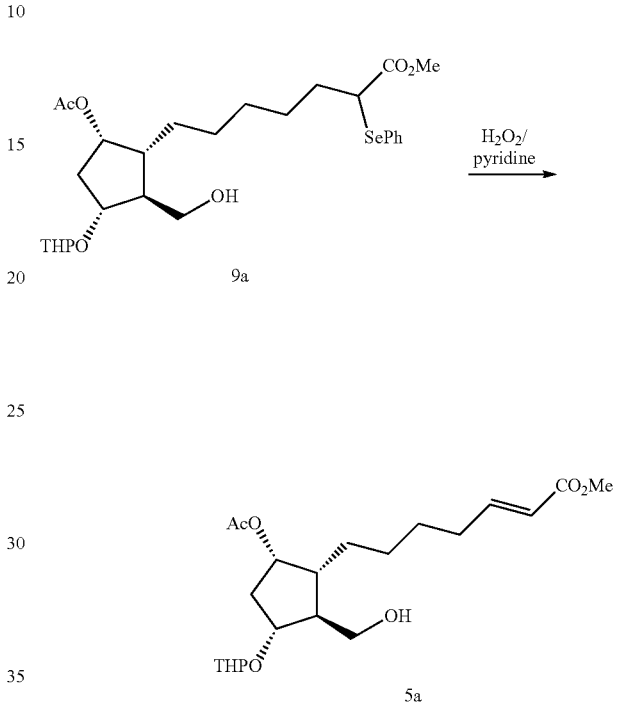

To compound (9a) (14.1 g) obtained in Example 2 was added dichloromethane (211 mL) and the mixture was stirred. Pyridine (4.10 mL) and 30% aqueous hydrogen peroxide (10.4 mL) were added thereto and the mixture was stirred at 0° C. for 1 hr to give a reaction mixture. The reaction mixture was diluted with dichloromethane, distilled water was added, and the mixture was extracted with dichloromethane. The obtained organic layer was washed with saturated brine, dried over anhydrous sodium sulfate, concentrated under reduced pressure, and purified by silica gel column chromatography using a mobile phase in which a gradient was applied from a mixed solution of hexane:ethyl acetate=3:1 (vol) to ethyl acetate, a mixed solution of ethyl acetate:methanol=20:1 (vol) to give compound (5a) (9.06 g).

$^1$H NMR (300 MHz, $CDCl_3$) δ6.94 (dt, J=15.6, 6.9 Hz, 1H), 5.80 (d, J=15.6 Hz, 1H), 5.07 (m, 1H), 4.72 (m, 0.55H), 4.54 (m, 0.45H), 4.15-4.04 (m, 1H), 4.04-3.88 (m, 1H), 3.88-3.73 (m, 2H), 3.66 (s, 3H), 3.60-3.48 (m, 2H), 2.04 (t, J=7.5 Hz, 2H), 1.95-1.15 (m, 18H).

Example 4

Production of methyl (2E)-7-((1R,2R,3R,5S)-5-acetoxy-2-((1E,4S)-7-cyclopropyl-4-methyl-3-oxohept-1-en-6-yn-1-yl)-3-((tetrahydro-2H-pyran-2-yl)oxy)cyclopentyl)hept-2-enoate (Compound (4a)) (Step 4)

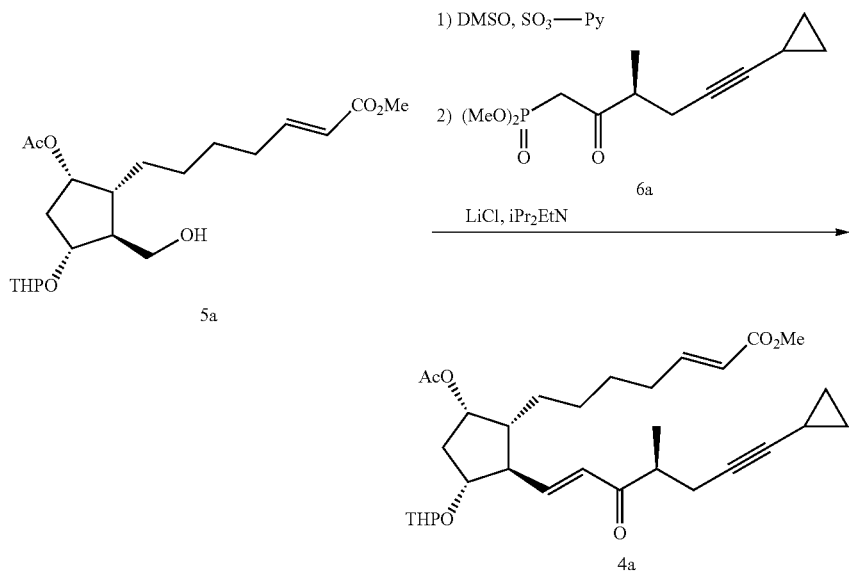

Compound (5a) (9.06 g) obtained in Example 3 was dissolved in ethyl acetate (146 mL), and the solution was cooled to −10° C. N,N-diisopropylethylamine (iPr$_2$EtN) (23.8 mL) was added thereto, a solution of SO$_3$-pyridine (SO$_3$—Py) (10.9 g) in DMSO (27.2 mL) was added and the mixture was stirred at −10° C. for 30 min to give the first mixture. To the first mixture were poured ethyl acetate (226 mL) and 1N hydrochloric acid (90.6 mL), and the mixture was partitioned by adding water.

The obtained first organic layer was concentrated under reduced pressure. To the composition obtained by concentration under reduced pressure was added hexane, and the mixture was successively washed with aqueous copper sulfate solution, saturated brine and water, and the thus-obtained second organic layer was dried over anhydrous sodium sulfate and concentrated under reduced pressure to give an aldehyde corresponding to compound (5a) (methyl 7-((1R,2R,3R,5S)-5-acetoxy-2-formyl-3-((tetrahydro-2H-pyran-2-yl)oxy)cyclopentyl)heptanoate) (8.6 g).

Lithium chloride (1.10 g) was heated to 170° C., dried under reduced pressure, and acetonitrile (43.2 mL) was added thereto. A solution of compound (6a) (6.69 g) synthesized as in Reference Example 2 in acetonitrile (86.4 mL) and N,N-diisopropylethylamine (iPr$_2$EtN) (3.76 mL) were added dropwise thereto and the mixture was stirred at 25° C. for 1 hr. A solution of the above-mentioned aldehyde (8.6 g) corresponding to compound (5a) in acetonitrile (86.4 mL) was added dropwise thereto, and the mixture was stirred at the same temperature for 15 hr to give the second mixture. To the second mixture were added ethyl acetate (103 mL) and saturated aqueous ammonium chloride solution (103 mL) and the mixture was partitioned by diluting with water. The aqueous layer was extracted with ethyl acetate. The obtained third organic layer was dried over anhydrous sodium sulfate, concentrated under reduced pressure, and purified by silica gel column chromatography using a mobile phase in which a gradient was applied from a mixed solution of hexane:ethyl acetate=86:14 (vol) to ethyl acetate to give compound (4a) (8.13 g) as a colorless oil. The yield in the reaction to obtain compound (4a) from compound (5a) was 61%.

$^1$H NMR (400 MHz, CDCl$_3$) δ6.92 (dt, J=15.6, 6.9 Hz, 1H), δ6.80-6.68 (m, 1H), δ6.32-6.24 (m, 1H), 5.79 (d, J=15.6 Hz, 1H), 5.12 (brt, J=5.7 Hz, 1H), 4.54 (dt, J=12.8, 3.0 Hz, 1H), 4.12-3.96 (m, 1H), 3.83-3.58 (m, 2H), 3.65 (s, 3H), 3.50-3.38 (m, 1H), 3.14-2.83 (m, 1H), 2.75-2.16 (m, 5H), 2.06 (s, 3H), 1.95-1.05 (m, 22H), 1.18 (d, J=7.2 Hz, 3H), 0.75-0.54 (m, 4H).

Example 5

Production of methyl (2E)-7-((1R,2R,3R,5S)-5-acetoxy-2-((1E,3S,4S)-7-cyclopropyl-3-hydroxy-4-methylhept-1-en-6-yn-1-yl)-3-hydroxycyclopentyl)hept-2-enoate (Compound (3a)) (Step 5)

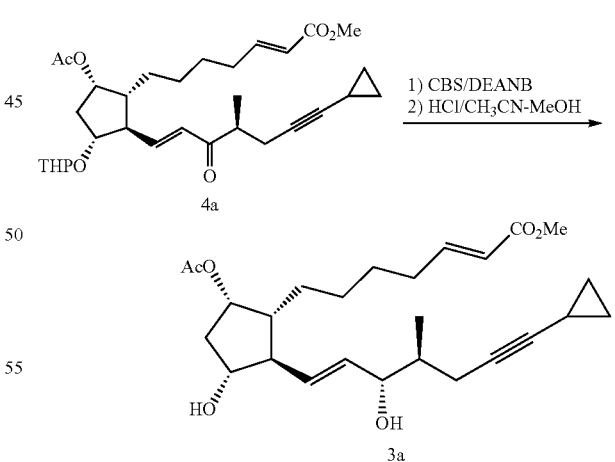

Compound (4a) (8.13 g) obtained in Example 4 was dissolved in toluene (58.4 mL), 1M toluene solution of R-(+)-2-methyloxazaborolidine (CBS) was added thereto, and the mixture was stirred under ice-cooling (−10° C. to 5° C.) for 30 min. Diethylaniline borane (DEANB) (2.79 mL) was added dropwise, and the mixture was stirred under ice-cooling (−10° C. to 5° C.) for 15 hr to give a mixture.

The mixture was diluted with ethyl acetate, methanol (3.1 mL) was added, and the mixture was partitioned by adding 1N hydrochloric acid and water. The obtained aqueous layer was extracted with ethyl acetate. The obtained organic layers were combined, washed with saturated brine, dried over anhydrous sodium sulfate, and concentrated under reduced pressure to give compound (3a) as a crude product (6.53 g).

The crude product (6.53 g) of the obtained compound (3a), acetonitrile (24.3 mL) and methanol (12.1 mL) were added thereto and dissolved, 0.1N hydrochloric acid (12.2 mL) was added and the mixture was stirred at 35° C. for 3 hr. 0.1N Aqueous sodium hydrogen carbonate solution (12.2 mL) and water were added thereto and the mixture was extracted with ethyl acetate. The obtained organic layer was washed with saturated brine, dried over anhydrous magnesium sulfate, and concentrated under reduced pressure. The composition obtained by concentrated under reduced pressure was purified by silica gel column chromatography using a mobile phase in which a gradient was applied from a mixed solution of hexane:ethyl acetate=67:33 (vol) to ethyl acetate to give compound (3a) (6.35 g) and a stereoisomer thereof (compound with reverse configuration of the 15-position hydroxy group) (0.70 g).

$^1$H NMR (400 MHz, CDCl$_3$) δ6.93 (dt, J=15.6, 6.9 Hz, 1H), 5.80 (d, J=15.6 Hz, 1H), 55.65-5.45 (m, 2H), 5.15 (brs, 1H), 4.14-3.85 (m, 2H), 3.73 (s, 3H), 2.60-2.30 (m, 1H), 2.28 (t, J=7.6 Hz, 2H), 2.30-2.13 (m, 2H), 2.04 (s, 3H), 1.85-1.10 (m, 12H), 0.96 (m, 3H), 0.72-0.58 (m, 4H).

Example 6

Production of (2E)-7-((1R,2R,3R,5S)-2-((1E,3S,4S)-7-cyclopropyl-4-methyl-3-((tetrahydro-2H-pyran-2-yl)oxy)hept-1-en-6-yn-1-yl)-5-hydroxy-3-((tetrahydro-2H-pyran-2-yl)oxy)cyclopentyl)hept-2-enoic acid (Compound (1a)) (Step 6)

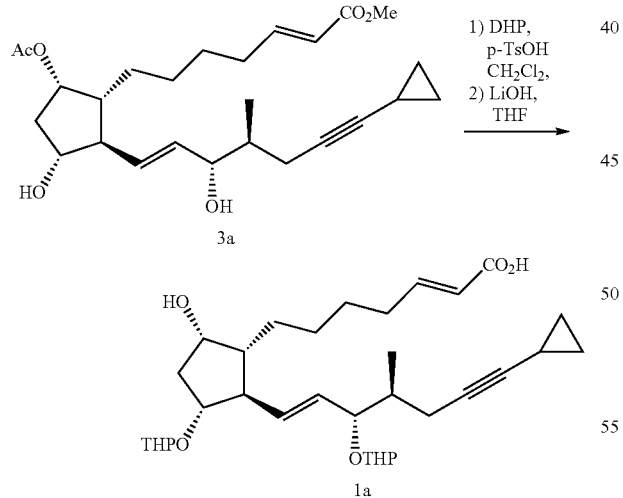

Compound (3a) (5.22 g) obtained in Example 5 was dissolved in dichloromethane (75.7 mL), 3,4-dihydro-2H-pyran (DHP) (3.22 mL) and p-toluenesulfonic acid monohydrate (p-TsOH. H$_2$O) (56.6 mg) were added thereto at 0° C., and the mixture was stirred at the same temperature for 30 min to give the first mixture. The first mixture was partitioned by adding dichloromethane (75.7 mL) and water (83.5 mL). The obtained aqueous layer was extracted with dichloromethane. The obtained organic layers were combined, dried over anhydrous sodium sulfate, and concentrated under reduced pressure to give compound (3a) in which a hydroxy group was protected by THP (hereinafter to be referred to as compound (3a')) as a crude product (7.19 g).

The above-mentioned crude product (7.19 g) of compound (3a') was dissolved in THF (46.0 mL), lithium hydroxide monohydrate (4.91 g) was added thereto, and the mixture was heated to 40° C. and stirred for 15 hr to give the second mixture. The second mixture was diluted with ethyl acetate (46.0 mL), 1N hydrochloric acid was added and the mixture was extracted with ethyl acetate. The obtained organic layer was dried over anhydrous magnesium sulfate, concentrated under reduced pressure, and purified by silica gel column chromatography using a mobile phase in which a gradient was applied from a mixed solution of hexane:ethyl acetate=1:1 (vol) to a mixed solution of hexane:ethyl acetate=1:3 (vol) to give compound (1a) (5.21 g).

$^1$H NMR (400 MHz, CDCl$_3$) δ7.00-6.87 (m, 1H), 5.81 (d, J=14.8 Hz, 1H), 5.63-5.41, 5.30-5.18 (m, 2H), 4.82-4.60 (m, 2H), 4.13-3.75 (m, 6H), 3.53-3.39 (m, 2H), 2.59-1.00 (m, 28H), 0.92 (m, 3H), 0.74-0.63 (m, 2H), 0.60-0.52 (m, 2H).

Example 7

Production of (2E)-7-((1R,2R,3R)-2-((1E,3S,4S)-7-cyclopropyl-3-hydroxy-4-methylhept-1-en-6-yn-1-yl)-3-hydroxy-5-oxocyclopentyl)hept-2-enoic acid (Compound (2a)) (Step 7)

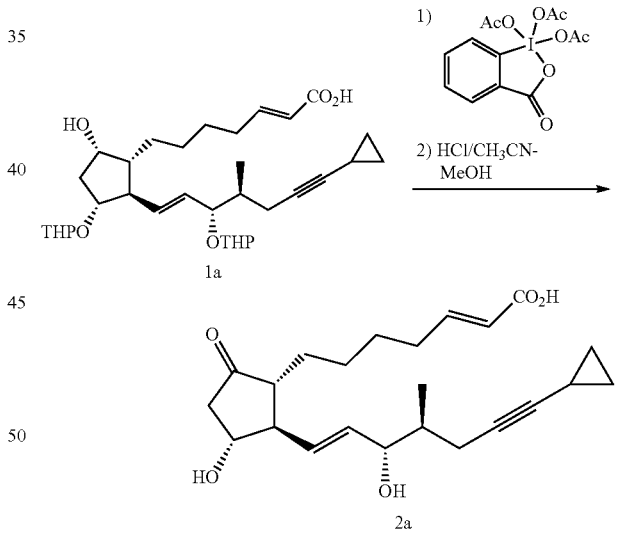

Compound (1a) (5.21 g) obtained in Example 6 was dissolved in dichloromethane (52.2 mL), 1,1,1-triacetoxy-1,1-dihydro-1,2-benziodoxol-3(1H)-one (Dess-Martin periodinane; Dess-Martin reagent) (4.55 g) was added thereto, and the mixture was stirred at room temperature for 1 hr to give the first mixture. The first mixture was diluted with dichloromethane (52.3 mL), 1M aqueous sodium thiosulfuric acid solution was added, and the mixture was stirred for 2 hr and partitioned by adding water. The obtained aqueous layer was extracted with dichloromethane, and the obtained organic layers were combined and washed successively with water and brine. The mixture was dried over anhydrous magnesium sulfate and concentrated under reduced pressure to give a carbonyl form of compound (1a) as a crude product (4.69 g).

The above-mentioned crude product (4.69 g) of the carbonyl form of compound (1a) was dissolved in acetonitrile (16.6 mL) and methanol (8.31 mL), 0.1N hydrochloric acid (8.31 mL) was added thereto, and the mixture was stirred at 35° C. for 3 hr to give the second mixture. To the second mixture were added 0.1N aqueous sodium hydrogen carbonate solution (8.31 mL) and water, and the mixture was extracted with ethyl acetate. The obtained organic layer was washed with saturated brine, dried over anhydrous magnesium sulfate, and concentrated under reduced pressure. The composition obtained by concentrated under reduced pressure was purified by silica gel column chromatography using a mobile phase in which a gradient was applied from a mixed solution of hexane:ethyl acetate=1:2 (vol) to ethyl acetate and to a mixed solution of ethyl acetate:methanol =20:1 (vol) to give compound (2a) (2.94 g).

$^1$H NMR (400 MHz, CDCl$_3$) δ6.98 (dt, J=15.6, 6.9 Hz, 1H), 5.81 (d, J=15.6 Hz, 1H), 5.66 (brs, 2H), 4.05-3.93 (m, 2H), 2.71 (dd, J=18.2, 7.4 Hz, 1H), 2.40-1.00 (m, 16H), 0.89 (d, J=6.8 Hz, 3H), 0.71-0.67 (m, 2H), 0.59-0.55 (m, 2H).

INDUSTRIAL APPLICABILITY

The present invention can provide a method for producing a novel compound (2) or a pharmaceutically acceptable salt thereof, which is useful as a blood flow improving agent, in a good yield.

Compound (3) and compound (4) according to the present invention are useful as synthetic intermediates for producing compound (2) or a pharmaceutically acceptable salt thereof.

Furthermore, the production method of the present invention is useful as an industrial-scale synthetic method since the method can be carried out by convenient operations via compounds easy to handle.

This application is based on a patent application No. 2017-210311 filed in Japan, the contents of which are incorporated in full herein.

The invention claimed is:

1. A compound represented by the formula 3:

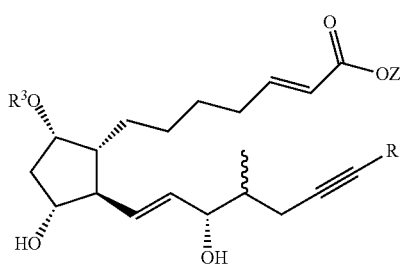

formula 3 wherein, in the formula 3, R is an alkyl group having 2 to 3 carbon atoms, a substituted alkyl group having 2 to 3 carbon atoms, a cycloalkyl group having 3 to 5 carbon atoms, or a substituted cycloalkyl group having 3 to 5 carbon atoms;

R$^3$ is a hydroxy-protecting group;

a methyl group bonded by a wavy line is a methyl group having α-configuration, β-configuration or a mixed configuration of α-configuration and β-configuration; and Z is an alkyl group having 1 to 4 carbon atoms or a substituted alkyl group having 1 to 4 carbon atoms.

2. A method for producing a compound represented by the formula 1 or a pharmaceutically acceptable salt thereof, comprising protecting a hydroxy group of a compound represented by the formula 3, and converting same to a compound represented by the formula 1 by subsequently removing R$^3$ and hydrolyzing a CO$_2$Z group:

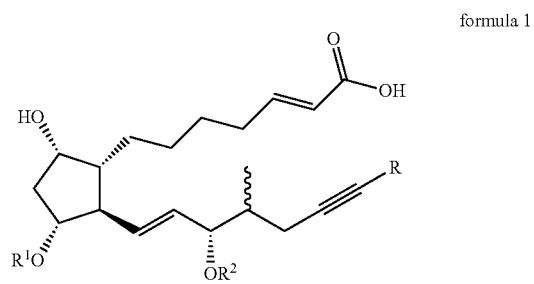

formula 1 wherein, in the formula 1, R is an alkyl group having 2 to 3 carbon atoms, a substituted alkyl group having 2 to 3 carbon atoms, a cycloalkyl group having 3 to 5 carbon atoms or a substituted cycloalkyl group having 3 to 5 carbon atoms;

R$^1$ and R$^2$ are each independently a hydroxy-protecting group; and a methyl group bonded by a wavy line is a methyl group having α-configuration, β-configuration or a mixed configuration of α-configuration and β-configuration,

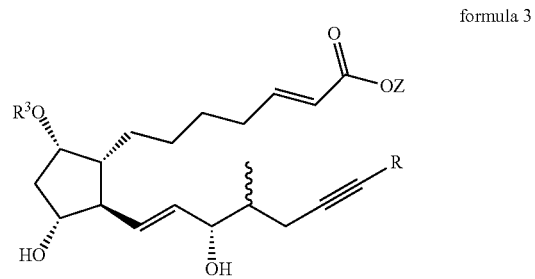

formula 3 wherein, in the formula 3, R$^3$ is a hydroxy-protecting group different from R$^1$ and R$^2$;

Z is an alkyl group having 1 to 4 carbon atoms or a substituted alkyl group having 1 to 4 carbon atoms; and R and a methyl group bonded by a wavy line are as defined above.

3. A method for producing a compound represented by the formula 2 or a pharmaceutically acceptable salt thereof, comprising oxidizing a hydroxy group of the compound represented by the formula 1 or a pharmaceutically acceptable salt thereof according to claim 2, and removing R$^1$ and R$^2$:

formula 2

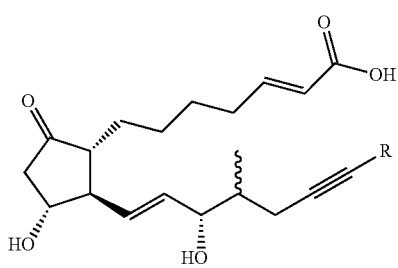

wherein, in the formula 2, R and a methyl group bonded by a wavy line are as defined in claim 2.

4. The production method according to claim 2, wherein the compound represented by the formula 3 is produced by reducing a carbonyl group of a compound represented by the formula 4 and then removing $R^4$:

formula 4

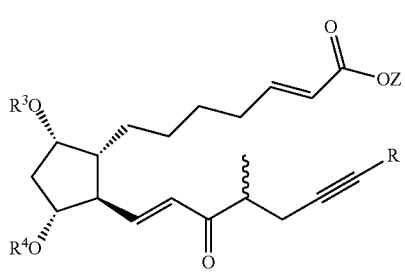

wherein, in the formula 4, $R^3$, R, a methyl group bonded by a wavy line and Z are as defined in claim 2; and $R^4$ is a hydroxy-protecting group different from $R^3$.

5. The production method according to claim 4, wherein the compound represented by the formula 4 is obtained by oxidizing a hydroxy group of the compound represented by the formula 5 to convert same to the corresponding aldehyde, and reacting the compound with a compound represented by the formula 6:

formula 5

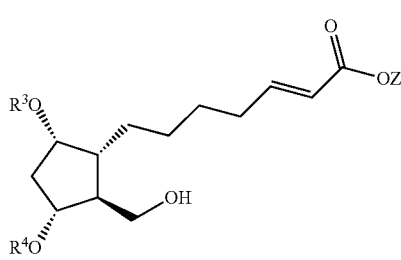

wherein, in the formula 5, $R^3$, $R^4$, and Z are as defined in claim 4, formula 6

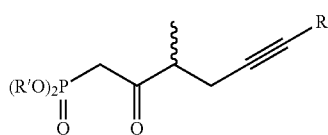

wherein, in the formula 6, R' is an alkyl group having 1 to 4 carbon atoms, and R and a methyl group bonded by a wavy line are as defined in claim 4.

6. The production method according to claim 5, wherein a compound represented by the formula 5 is obtained by arylselenylating a compound represented by the formula 7 to convert same to a compound represented by the formula 8, protecting a hydroxy group, removing $R^5$ to convert the compound to a compound represented by the formula 9, and oxidatively eliminating an arylselenyl group to introduce a double bond:

formula 7

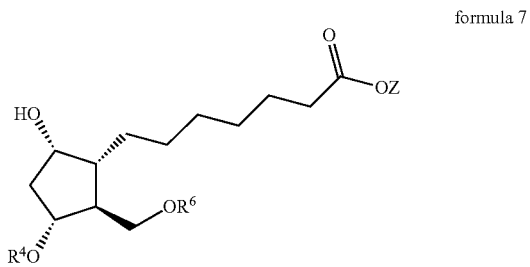

wherein, in the formula 7, $R^4$ and Z are as defined in claim 5; and $R^5$ is a hydroxy-protecting group different from $R^3$ and $R^4$, formula 8

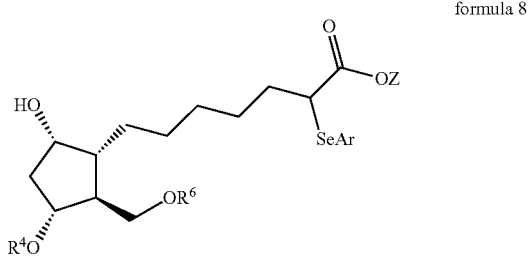

wherein, in the formula 8, $R^4$, $R^5$ and Z are as defined above; and

Ar is an aryl group or a substituted aryl group, formula 9

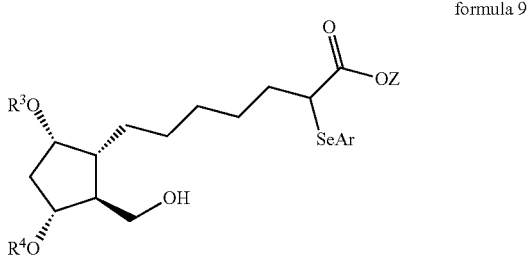

wherein, in the formula 9, $R^3$ is as defined in claim 5; and $R^4$, Ar and Z are as defined above.

7. A compound represented by the formula 4,

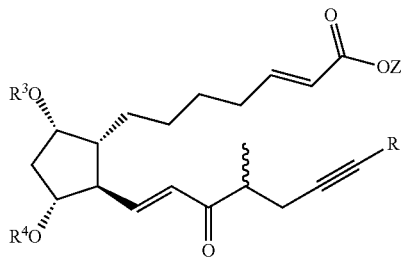

formula 4 wherein, in the formula 4, R is an alkyl group having 2 to 3 carbon atoms, a substituted alkyl group having 2 to 3 carbon atoms, a cycloalkyl group having 3 to 5 carbon atoms, or a substituted cycloalkyl group having 3 to 5 carbon atoms;

$R^3$ is a hydroxy-protecting group;

$R^4$ is a hydroxy-protecting group different from $R^3$;

a methyl group bonded by a wavy line is a methyl group having α-configuration, β-configuration or a mixed configuration of α-configuration and α-configuration; and Z is an alkyl group having 1 to 4 carbon atoms or a substituted alkyl group having 1 to 4 carbon atoms.

8. A method for producing a compound represented by the formula 3, comprising reducing a carbonyl group of the compound represented by the formula 4, and removing $R^4$:

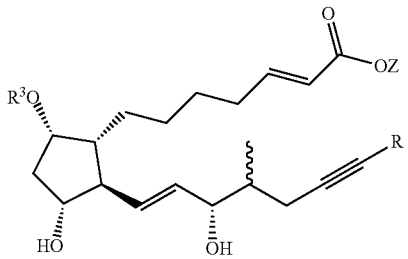

formula 3 wherein, in the formula 3, R is an alkyl group having 2 to 3 carbon atoms, a substituted alkyl group having 2 to 3 carbon atoms, a cycloalkyl group having 3 to 5 carbon atoms, or a substituted cycloalkyl group having 3 to 5 carbon atoms;

$R^3$ is a hydroxy-protecting group;

a methyl group bonded by a wavy line is a methyl group having α-configuration, β-configuration or a mixed configuration of α-configuration and β-configuration; and Z is an alkyl group having 1 to 4 carbon atoms or a substituted alkyl group having 1 to 4 carbon atoms,

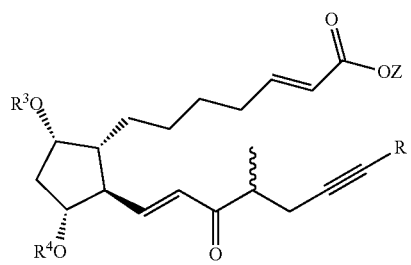

formula 4 wherein, in the formula 4, $R^3$, R, a methyl group bonded by a wavy line, and Z are as defined above; and $R^4$ is a hydroxy-protecting group different from $R^3$.

9. A method for producing a compound represented by the formula 4, comprising oxidizing a hydroxy group of a compound represented by the formula 5 to convert the compound to the corresponding aldehyde, and reacting same with a compound represented by the formula 6

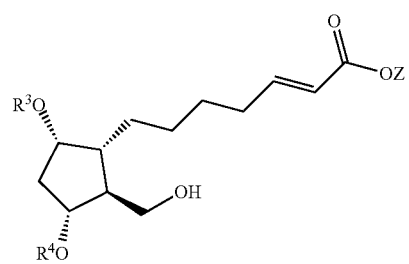

formula 5 wherein, in the formula 5, $R^3$ is a hydroxy-protecting group;

$R^4$ is a hydroxy-protecting group different from $R^3$; and

Z is an alkyl group having 1 to 4 carbon atoms or a substituted alkyl group having 1 to 4 carbon atoms,

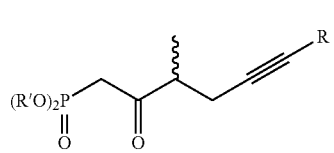

formula 6 wherein, in the formula 6, R' is an alkyl group having 1 to 4 carbon atoms, R is an alkyl group having 2 to 3 carbon atoms, a substituted alkyl group having 2 to 3 carbon atoms, a cycloalkyl group having 3 to 5 carbon atoms, or a substituted cycloalkyl group having 3 to 5 carbon atoms, and a methyl group bonded by a wavy line is a methyl group having α-configuration, β-configuration or a mixed configuration of α-configuration and β-configuration, formula 4

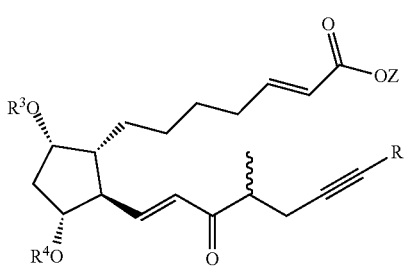

wherein, in the formula 4, $R^3$, $R^4$, R, a methyl group bonded by a wavy line, and Z are as defined above.

10. A method for producing a compound represented by the formula 2 or a pharmaceutically acceptable salt thereof, comprising arylselenylating a compound represented by the formula 7 to convert same to a compound represented by the formula 8, protecting a hydroxy group of the compound represented by the formula 8, removing $R^5$ to convert the compound to a compound represented by the formula 9, oxidatively eliminating an arylselenyl group of the compound represented by the formula 9 to introduce a double bond and convert the compound to a compound represented by the formula 5, oxidizing a hydroxy group of the compound represented by the formula 5 to convert same to the corresponding aldehyde, reacting same with a compound represented by the formula 6 to convert the compound to a compound represented by the formula 4, reducing a carbonyl group of the compound represented by the formula 4, removing $R^4$ to convert the compound to a compound represented by the formula 3, protecting a hydroxy group of the compound represented by the formula 3, subsequently removing $R^3$ and hydrolyzing a $CO_2Z$ group to convert the compound to a compound represented by the formula 1 or a pharmaceutically acceptable salt thereof, and oxidizing a hydroxy group of the compound represented by the formula 1 or a pharmaceutically acceptable salt thereof, and removing $R^1$ and $R^2$ to convert the compound to a compound represented by the formula 2 or a pharmaceutically acceptable salt thereof, formula 2

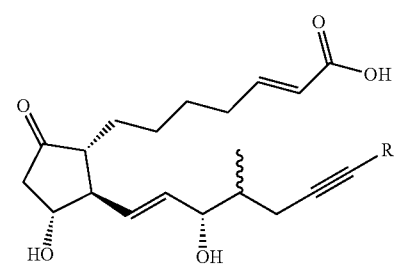

wherein, in the formula 2, R is an alkyl group having 2 to 3 carbon atoms, a substituted alkyl group having 2 to 3 carbon atoms, a cycloalkyl group having 3 to 5 carbon atoms or a substituted cycloalkyl group having 3 to 5 carbon atoms; and a methyl group bonded by a wavy line is a methyl group having α-configuration, β-configuration or a mixed configuration of α-configuration and β-configuration, formula 7

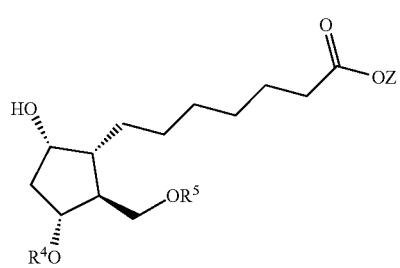

wherein, in the formula 7, Z is an alkyl group having 1 to 4 carbon atoms or a substituted alkyl group having 1 to 4 carbon atoms;

$R^4$ is a hydroxy-protecting group; and $R^5$ is a hydroxy-protecting group different from $R^3$ and $R^4$, formula 8

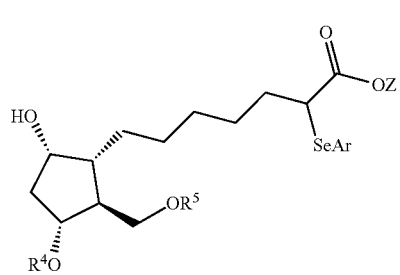

wherein, in the formula 8, $R^4$, $R^5$ and Z are as defined above; and

Ar is an aryl group or a substituted aryl group, formula 9

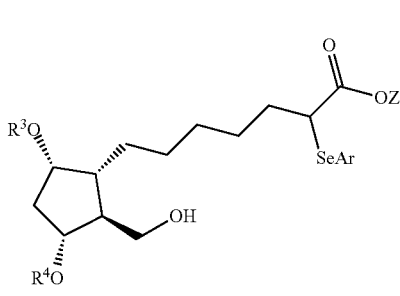

wherein, in the formula 9, $R^4$, Ar and Z are as defined above; and $R^3$ is a hydroxy-protecting group different from $R^4$,

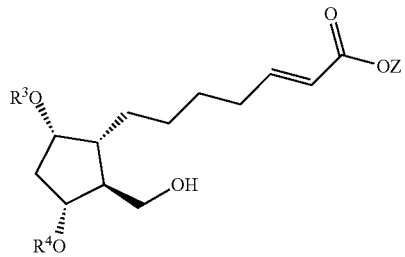

formula 5 wherein, in the formula 5, $R^3$, $R^4$ and Z are as defined above,

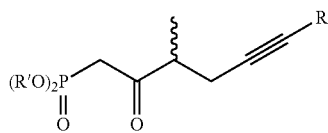

formula 6 wherein, in the formula 6, R' is an alkyl group having 1 to 4 carbon atoms, and R and a methyl group bonded by a wavy line are as defined above,

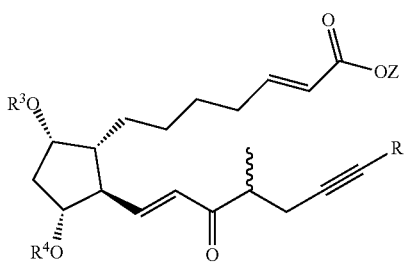

formula 4 wherein, in the formula 4, R, $R^3$, $R^4$, a methyl group bonded by a wavy line and Z are as defined above,

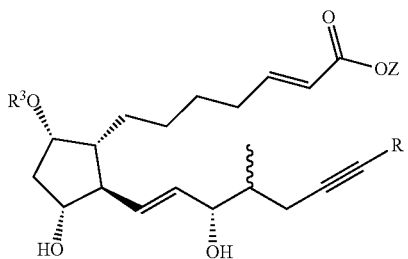

formula 3 wherein, in the formula 3, R, $R^3$, a methyl group bonded by a wavy line and Z are as defined above,

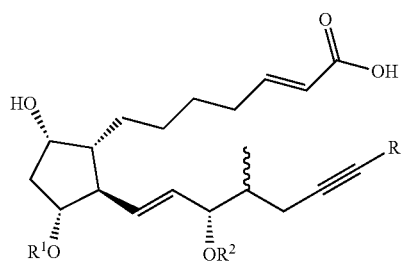

formula 1 wherein, in the formula 1, $R^1$ and $R^2$ are each independently a hydroxy-protecting group; and R and a methyl group bonded by a wavy line, are as defined above.

11. The compound according to claim 1, wherein, in the formula 3, the methyl group bonded by a wavy line is as defined in claim 1, R is an ethyl group or a cyclopropyl group, $R^3$ is an acetyl group, and Z is a methyl group.

12. The compound according to claim 7, wherein, in the formula 4, the methyl group bonded by a wavy line is as defined in claim 7, R is an ethyl group or a cyclopropyl group, $R^3$ is an acetyl group, $R^4$ is a 2-tetrahydropyranyl group, and Z is a methyl group.

13. The compound according to claim 2, wherein the methyl group bonded by a wavy line in the formula 1 is as defined in claim 2, R is an ethyl group or a cyclopropyl group, $R^1$ and $R^2$ are each a 2-tetrahydropyranyl group, the methyl group bonded by a wavy line in the formula 3 is as defined in claim 2, R is as defined in the formula 1, $R^3$ is an acetyl group, and Z is a methyl group.

* * * * *